US006872549B2

(12) United States Patent
Van Ness et al.

(10) Patent No.: US 6,872,549 B2
(45) Date of Patent: Mar. 29, 2005

(54) METHODS FOR INCREASING POLYPEPTIDE PRODUCTION

(75) Inventors: Kirk P. Van Ness, Seattle, WA (US); Michael T. Trentalange, Seattle, WA (US); Bradley D. Dell, Seattle, WA (US); Jeffrey T. McGrew, Seattle, WA (US)

(73) Assignee: Immunex Corporation, Thousand Oaks, CA (US)

( * ) Notice: Subject to any disclaimer, the term of this patent is extended or adjusted under 35 U.S.C. 154(b) by 48 days.

(21) Appl. No.: 10/400,334

(22) Filed: Mar. 27, 2003

(65) Prior Publication Data

US 2003/0211579 A1 Nov. 13, 2003

Related U.S. Application Data

(60) Provisional application No. 60/368,246, filed on Mar. 27, 2002, and provisional application No. 60/368,248, filed on Mar. 27, 2002.

(51) Int. Cl.[7] ............................................... C12P 21/02
(52) U.S. Cl. ....................... 435/69.1; 435/358; 435/377
(58) Field of Search ............................... 435/69.1, 377, 435/358

(56) References Cited

U.S. PATENT DOCUMENTS

| | | | |
|---|---|---|---|
| 3,824,286 A | 7/1974 | Grimmelikhuysen et al. | |
| 4,266,024 A | 5/1981 | Swetly et al. | |
| 4,301,249 A | * 11/1981 | Markus et al. ............ | 435/235.1 |
| 4,357,422 A | 11/1982 | Giard et al. | |
| 4,416,986 A | 11/1983 | Markus et al. | |
| 4,473,647 A | 9/1984 | Carpenter et al. | |
| 4,992,472 A | 2/1991 | Driscoll et al. | |
| 5,055,608 A | 10/1991 | Marks et al. | |
| 5,330,744 A | 7/1994 | Pontremoli et al. | |
| 5,674,834 A | 10/1997 | Theofan et al. | |
| 5,705,364 A | 1/1998 | Etcheverry et al. | |
| 5,712,163 A | 1/1998 | Parenteau et al. | |
| 6,506,598 B1 | 1/2003 | Andersen et al. | |
| 2001/0010922 A1 | 8/2001 | Dalla-Favera et al. | |

FOREIGN PATENT DOCUMENTS

| | | |
|---|---|---|
| EP | 0 373 623 | 6/1990 |
| EP | 0 764 719 | 3/1997 |
| WO | WO 98/28010 | 7/1998 |
| WO | WO 99/32605 | 7/1999 |
| WO | WO 00/20576 | 4/2000 |

OTHER PUBLICATIONS

Beavo JA et al., "Effects of Xanthine derivatives on lipolysis and on adenosine 3', 5'-monophosphate phosphodiesterase activity, " *Mol Pharmacol* Nov. 1970; 6(6):597–603.
Carrasco L et al., "Antibiotics and compounds affecting translation by eukaryotic ribosomes, specific enhancement of aminoacyl–tRNA binding by methylxanthines," *Mol Cell Biochem* Feb. 1976; 10(2):97–122.

Cosgrove DE and Cox GS, "Enhancement by theophylline of the butyrate–mediated induction of choriogonadotropin α–subunit in HeLa cells," *Arch Biochem Biophys* Jul. 1990; 280(1):95–102.
Fernandez–Puentes C et al., "The enhancement of polypeptide synthesis in mammalian systems by methylxanthines," *FEBS Lett* Sep. 1974; 45(1):132–135.
Kaufmann H et al., "Comparative analysis of two controlled proliferation strategies regarding product quality, influence on tetracycline–regulated gene expression, and productivity," *Biotechnol Bioeng* 2001; 72(6):592–602.
Kaufmann H et al., "Influence of low temperature on productivity, proteome and protein phosphorylation of CHO cells," *Biotechnol Bioeng* 1999; 63:573–582.
Marks PA et al., "Inducing differentiation of transformed cells with hybrid polar compounds: a cell cycle–dependent process," *Proc Natl Acad Sci USA* Oct. 1994; 91:10251–10254.
Montague W and Cook JR, "Adenosine 3':5'–cyclic monophosphate and insulin release," *Biochem J* Dec. 1970; 120(4):9P–10P.
Montague W and Cook JR, "The role of adenosine 3':5'–cyclic monophosphate in the regulation of insulin release by isolated rat islets of langerhans," *Biochem J* 1971; 122:115–120.
Paterson T et al., "Approaches to maximizing stable expression of $\alpha_1$–antitrypsin in transformed CHO cells," *Appl Microbiol Biotechnol* 1994; 40:691–698.
Rajaraman R and Faulkner G, "Reverse transformation of chinese hamster ovary cells by methyl xanthines," *Exp Cell Res* 1984; 154:342–356.
Reuben RC et al., "A new group of potent inducers of differentiation in murine erythroleukemia cells," *Proc Natl Acad Sci USA* Mar. 1976; 73(3):862–866.
Richon VM et al., "A class of hybrid polar inducers of transformed cell differentiation inhibits histone deacetylases," *Proc Natl Acad Sci USA* Mar. 1998; 95:3003–3007.
Sarkaria JN et al., "Inhibition of ATM and ATR kinase activities by the radiosensitizing agent, caffeine," *Cancer Res* Sep. 1999; 59:4375–4382.
Schlegel R et al., "Exposure to caffeine and suppression of DNA replication combine to stabilize the proteins and RNA required for premature mitotic events," *J Cell Physiol* 1987; 131:85–91.
Staak K et al., "Pentoxifylline promotes replication of human cytomegalovirus in vivo and in vitro," *Blood* May 15, 1997; 89(10):3682–3690.

(List continued on next page.)

*Primary Examiner*—James Ketter
(74) *Attorney, Agent, or Firm*—Rosemary Sweeney

(57) ABSTRACT

The invention provides methods of increasing the production of polypeptides, optionally recombinant polypeptides, from mammalian cells using xanthine derivatives or hybrid polar compounds and cultures containing the same. Combinations of inducers including a hybrid polar compound and/or a xanthine derivative and/or an alkanoic acid can also be used, optionally at temperatures less than 37° C.

69 Claims, 4 Drawing Sheets

OTHER PUBLICATIONS

Tachibana H et al., "Induction of light chain replacement in human plasma cells by caffeine is independent from both the upregulation of RAG protein expression and germ line transcription," *J Biol Chem* Feb. 25, 2000; 275(8):5927–5933.

Takahashi K et al., "Growth rate suppression of cultured mammalian cells enhances protein productivity," *Cytotechnol* 1994; 15:57–64.

Tamura RN and Cox GS, "Enhancement by theophylline of the butyrate–mediated induction of choriogonadotropin α–subunit in HeLa cells," *Arch Biochem Biophys* Jul. 1990; 280(1):87–94.

Taylor WR and Stark GR, "Regulation of the G2/M transition by p53," *Oncogene* 2001; 20:1803–1815.

Zoumpourlis V and Spandidos DA, "Hexamethylene bisacetamide stimulates the expression of human immunodeficiency virus long terminal repeat sequences in rat and human fibroblasts," *Anti–Cancer Drugs* 1992; 3:163–167.

* cited by examiner

US 6,872,549 B2

METHODS FOR INCREASING POLYPEPTIDE PRODUCTION

This application claims the benefit of U.S. Provisional Application Nos. 60/368,246 and 60/368,248, both filed Mar. 27, 2002, and both of which are incorporated herein in their entirety.

FIELD OF THE INVENTION

The invention is in the field of polypeptide production, particularly recombinant polypeptide production in cell culture.

BACKGROUND

Polypeptides are useful in a variety of diagnostic, therapeutic, agricultural, nutritional, and research applications. Although polypeptides can be isolated from natural sources, the isolation of large quantities of a specific polypeptide from natural sources may be expensive. Also, the polypeptide may not be of uniform quality due to variation in the source material. Recombinant DNA technology allows more uniform and cost-effective large-scale production of specific polypeptides.

One goal of recombinant polypeptide production is the optimization of culture conditions so as to obtain the greatest possible productivity. Incremental increases in productivity can be economically significant. Some of the methods to increase productivity in cell culture include using enriched medium, monitoring osmolarity during production, decreasing temperatures during specific phases of a cell culture, and/or the addition of sodium butyrate (see, e.g., U.S. Pat. No. 5,705,364).

However, as more polypeptide-based drugs demonstrate clinical effectiveness and increased commercial quantities are needed, available culture facilities become limited. Accordingly, there remains a need in the art to continually improve yields of recombinant polypeptides from each cell culture run.

SUMMARY

As shown by the experimental data reported herein, xanthine derivatives and/or hybrid polar compounds can dramatically induce the production of polypeptides, especially recombinant polypeptides, from mammalian cell lines. Moreover, xanthine derivatives and/or hybrid polar compounds can be used in combination with other induction methods to further increase polypeptide expression.

Thus, in one aspect, the invention provides a method for producing a polypeptide, which may be a recombinant polypeptide, comprising culturing a mammalian cell line in a growth phase followed by a production or induction phase, which can occur at a temperature of less than 37° C., and adding to the culture during the production phase a xanthine derivative. The addition of the xanthine derivative can increase the production of the polypeptide. The mammalian cell line can be a cell line that has been genetically engineered to produce the polypeptide or a hybridoma cell line that can produce an antibody. The xanthine derivative may be caffeine at a concentration from about 0.01 millimolar to about 5.0 millimolar or from about 0.01 millimolar to about 3.0 millimolar. In some embodiments, the mammalian cell line is a CHO cell line, and it may have been transformed with a recombinant vector encoding the recombinant polypeptide. Optionally, the vector can comprise a cytomegalovirus (CMV) promoter. Typically, the cell does not naturally express the polypeptide or only naturally expresses the polypeptide at very low levels (in the absence of genetic engineering). The polypeptide may be a recombinant fusion polypeptide or a human or humanized antibody. The production or induction phase can occur at a temperature from about 29° C. to about 36° C. or from about 30° C. to about 33° C. The growth phase can occur at a temperature from about 35° C. to about 38° C.

Optionally, at least two different xanthine derivatives can be added. The xanthine derivative(s) can be selected from the group consisting of caffeine, 3-isobutyl-1-methylxanthine, theophylline, theobromine, pentoxyphylline, and aminophylline or from a subset of this group. If two different xanthine derivatives are added, they can be caffeine and 3-isobutyl-1-methylxanthine. Xanthine derivatives can be added multiple times during the culturing of the cell line, and the cell line can be cultured in the presence of the xanthine derivative for at least about 5 days. The concentration of each xanthine derivative added to the culture can be from about 0.001 millimolar to about 3 millimolar. The recombinant polypeptide can be collected from the medium and formulated. The medium may further comprise a hybrid polar compound and/or an alkanoic acid. The hybrid polar compound can be hexamethylene bisacetamide, optionally at a concentration from about 0.1 millimolar to about 5 millimolar. The xanthine derivative can be caffeine, optionally at a concentration from about 0.1 millimolar to about 4 millimolar. The alkanoic acid can be a salt of butyric acid, optionally at a concentration from about 0.1 millimolar to about 2 millimolar. The mammalian cells can be cultured at a temperature from about 29° C. to about 36° C. or from about 30° C. to about 33° C. The mammalian cells can be cultured in a growth phase at a first temperature from about 35° C. to about 38° C. before they are shifted to a production phase at a second temperature from about 29° C. to about 36° C., wherein the second temperature can be lower than the first temperature. The xanthine can be added at the time of the shift from the first temperature to the second temperature and/or before and/or after the shift.

In another aspect the invention provides a method for producing a recombinant polypeptide comprising growing in culture a mammalian cell line, optionally a CHO cell line that has been genetically engineered to produce the recombinant polypeptide, and adding to the culture medium at least one xanthine derivative selected from the group consisting of theobromine and caffeine. The addition of the xanthine derivative can increase the production of the recombinant polypeptide. The mammalian cell line may have been transformed with a recombinant vector encoding the recombinant polypeptide. Optionally, the vector can comprise a cytomegalovirus (CMV) promoter. Typically, the cell line does not naturally express the recombinant polypeptide or only naturally expresses the recombinant polypeptide at very low levels (in the absence of genetic engineering). The recombinant polypeptide may be a recombinant fusion polypeptide or a human or humanized antibody. The cell line can be cultured in a growth phase, which is distinct from a production or induction phase. The production phase can occur at a temperature less than 37° C. The cell line can be cultured at a temperature of from about 29° C. to about 36° C. or from about 30° C. to about 33° C. Optionally, at least two different xanthine derivatives can be added. Xanthine derivatives can be added multiple times during the culturing of the cell line. The concentration of each xanthine derivative added to the culture can be from about 0.001 millimolar to about 3 millimolar. The recombinant polypeptide can be collected from the medium and formulated. The mammalian cell line can be cultured at a first temperature from about 35° C. to about 38° C. before it is shifted to a second temperature from about 29° C. to about 36° C., and the xanthine derivative can be added at the time of the shift from the first temperature to the second temperature and/or before and/or after the shift. The second temperature can be lower than the first temperature.

In another aspect, the invention provides a culture comprising a CHO cell genetically engineered to produce a polypeptide, a production medium, and at least one xanthine derivative selected from the group consisting of caffeine, 3-isobutyl-1-methylxanthine, theophylline, theobromine, pentoxyphylline, and aminophylline or from a subset of this group. The culture can comprise at least two xanthine derivatives. The concentration of each xanthine derivative present can be from about 0.001 millimolar to about 3 millimolar or from about 0.01 millimolar to about 3 millimolar. The culture can comprise serum-free medium, and may comprise no added protein or may comprise insulin or IGF-1. Additionally, the culture can comprise dimethylformamide, dimethylsulfoxide, or dimethylacetamide. The invention, because of its low cost and convenience, is particularly useful for large scale culturing of CHO cells. The culture can be a large scale culture of at least 100 liters, or even at least 500 liters, in size. The culture can comprise a homogeneous CHO cell line.

In still another aspect, the invention encompasses a culture comprising a CHO cell genetically engineered to produce a polypeptide, a production medium, and at least one xanthine derivative, wherein the culture is grown at less than 37° C. for at least part of its life. The xanthine derivative or derivatives present can be within the concentration range from about 0.001 millimolar to about 3 millimolar or from about 0.01 millimolar to about 3 millimolar, and the culture can contain at least two different xanthine derivatives. The xanthine derivatives can be selected from the group consisting of caffeine, 3-isobutyl-1-methylxanthine, theophylline, theobromine, pentoxyphylline, and aminophylline or from a subset of this group such as caffeine, theobromine and pentoxyphylline. The size of the culture can be at least 100 liters, and the production medium can be serum-free medium and can comprise either no added protein or insulin or IGF-1. The culture can comprise a homogeneous CHO cell line.

In a further aspect, the invention includes a method for producing a polypeptide in a culture of mammalian cells comprising incubating the culture at a temperature of about 37° C. and thereafter incubating the culture at a temperature from about 29° C. to 36° C., and adding to the culture a xanthine derivative during the incubation at a temperature from about 29° C. to 36° C., wherein the polypeptide is a recombinant polypeptide or an antibody. The xanthine derivative can be selected from the group consisting of caffeine, 3-isobutyl-1-methylxanthine, theophylline, theobromine, pentoxyphylline, and aminophylline or from a subset of this group such as caffeine, theobromine, and pentoxyphylline. The mammalian cells can be hybridoma cells or CHO cells. The xanthine derivative or derivatives present can be within the concentration range from about 0.001 millimolar to about 3 millimolar or from about 0.01 millimolar to about 3 millimolar, and the culture can contain at least two different xanthine derivatives. Xanthine derivatives can be added multiple times during the culturing of the cell line.

The invention provides a method for producing a recombinant polypeptide comprising culturing a mammalian cell line, in some embodiments a CHO cell line, at a temperature from about 29° C. to about 36° C., optionally at temperatures between about 29° C. and 35° C. or from about 30° C. to about 33° C., in a medium comprising a hybrid polar compound. The medium can be serum free. The addition of the hybrid polar compound can increase the production of the recombinant polypeptide. The hybrid polar compound can be hexamethylene bisacetamide, optionally at a concentration from about 0.1 millimolar to about 20 millimolar or from about 0.1 millimolar to about 5 millimolar. Furthermore, the medium may comprise an alkanoic acid, such as a salt of butyric acid, at a concentration, for example, from about 0.05 millimolar to about 10 millimolar, optionally from about 0.1 millimolar to about 2 millimolar. Furthermore, the medium may comprise a xanthine derivative, for example, caffeine, at a concentration from about 0.005 millimolar to 10 millimolar, optionally from about 0.01 millimolar to 4 millimolar or from about 0.1 millimolar to 4 millimolar. The mammalian cells can be cultured at a first temperature from about 35° C. to about 38° C. before they are shifted to a second temperature between about 29° C. and 36° C., and the hybrid polar compound can be added after the shift from the first temperature to the second temperature. The mammalian cells may be genetically engineered to produce a polypeptide, optionally a secreted polypeptide that can be recovered from the medium, including RANK:Fc, type II interleukin-1 receptor, TNFR:Fc, CD40 ligand, TRAIL, flt3-ligand, IL-4 receptor, G-CSF, erythropoietin, an antibody, or a substantially similar polypeptide, among others.

In another embodiment, the invention provides an improved method for producing a polypeptide by culturing mammalian cells comprising culturing the cells in a medium comprising a hybrid polar compound, optionally at temperatures from about 29° C. to about 36° C., between about 29° C. and 35° C., or from about 30° C. to about 33° C. The hybrid polar compound may be hexamethylene bisacetamide, optionally at a concentration between about 0.1 millimolar and about 5 millimolar. The addition of the hybrid polar compound can increase the production of the polypeptide, which may be a recombinant polypeptide. Furthermore, the medium may comprise an alkanoic acid, for example, butyric acid, optionally at a concentration from about 0.05 millimolar to about 10 millimolar or from about 0.1 millimolar to about 2 millimolar. Furthermore, the medium may comprise a xanthine, such as, for example, caffeine, optionally at a concentration from about 0.005 millimolar to 10 millimolar or from about 0.01 millimolar to 5 millimolar. Optionally, the polypeptide may be RANK:Fc, type II interleukin-1 receptor, TNFR:Fc, CD40 ligand, TRAIL, flt3-ligand, IL-4 receptor, GM-CSF, erythropoietin, an antibody, or a substantially similar polypeptide among others.

In another aspect, the invention provides a method for obtaining a polypeptide, optionally a recombinant polypeptide, comprising recovering the polypeptide from medium in which mammalian cells have been grown, wherein the mammalian cells can secrete the polypeptide and are grown at temperatures between about 29° C. and 35° C., optionally from about from about 30° C. to about 33° C., in medium comprising hexamethylene bisacetamide. The hexamethylene bisacetamide may be present at concentrations between about 0.1 millimolar and about 5 millimolar. Furthermore, the medium may comprise an alkanoic acid, for example, butyric acid, optionally at a concentration from about 0.05 millimolar to about 10 millimolar or from about 0.1 millimolar to about 2 millimolar. Furthermore, the medium may comprise a xanthine, for example, caffeine, optionally at a concentration from about 0.005 millimolar to 10 millimolar or from about about 0.01 millimolar to 5 millimolar. The polypeptide may be RANK:Fc, type II interleukin-1 receptor, TNFR:Fc, CD40 ligand, TRAIL, flt3-ligand, IL-4 receptor, G-CSF, erythropoietin, an antibody, or a substantially similar polypeptide, among others.

In a further embodiment, the invention comprises method for producing a recombinant polypeptide comprising culturing mammalian cells in a medium comprising a hybrid polar compound and a xanthine, wherein the mammalian cells have been genetically engineered to express the recombinant polypeptide. The medium may further comprise an alkanoic acid, such as, for example, a salt of butyric acid, which may be at a concentration from about 0.1 millimolar to about 2 millimolar. The hybrid polar compound can be hexamethylene bisacetamide, which may be at a concentration from about 0.1 millimolar to about 5 millimolar, and/or the xanthine can be caffeine, which may be at a concentration from about 0.1 millimolar to about 4 millimolar. The cells can be cultured at a temperature from about 29° C. to about 36° C. or from about 30° C. to about 33° C. The mammalian cells can be cultured at a first temperature from about 35° C. to about 38° C. before they are shifted to a second temperature from about 29° C. to about 36° C., and the hybrid polar compound and the xanthine can be added at the time of the shift from the first temperature to the second temperature and/or before and/or after the shift. The can be medium can be serum free.

In a further embodiment, the invention encompasses a method for producing a polypeptide, optionally a recombinant polypeptide, comprising culturing mammalian cells in a medium comprising a hybrid polar compound and an alkanoic acid, wherein the mammalian cells may have been genetically engineered to express the recombinant polypeptide. The hybrid polar compound can be hexamethylene bisacetamide, and the hybrid polar compound can be present at a concentration of from about 0.5 millimolar to about 10 millimolar or at a concentration between about 0.5 millimolar and 2.5 millimolar. The alkanoic acid can be a salt of butyric acid, and the alkanoic acid can be present at a concentration from about 0.1 millimolar to about 5 millimolar or at a concentration between about 0.1 millimolar and about 2.0 millimolar. The mammalian cells can be cultured at a temperature from about 29° C. to about 36° C., and the medium can be serum free. The mammalian cell line can be cultured at a first temperature from about 35° C. to about 38° C. before they are shifted to a second temperature from about 29° C. to about 36° C., and the hybrid polar compound and the alkanoic acid may be added after the shift from the first temperature to the second temperature. The medium can further comprise a xanthine derivative at a concentration from about 0.001 millimolar to about 5.0 millimolar. The mammalian cell line can be a hybridoma cell line or a CHO cell line.

In still another embodiment, the invention provides a method for producing a polypeptide comprising culturing a mammalian cell line in a production phase at a second temperature from about 30° C. to 34° C. in a medium comprising a hybrid polar compound, wherein the production phase follows a growth phase at a first temperature from about 35° C. to about 38° C. The polypeptide can be a recombinant polypeptide or an antibody. The hybrid polar compound can be hexamethylene bisacetamide, optionally at a concentration from about 0.1 millimolar to about 5 millimolar. The hybrid polar compound may be added after the shift from the first temperature to the second temperature. The medium can further comprise an alkanoic acid, which can be a salt of butyric acid, optionally at a concentration from about 0.05 millimolar to about 10.0 millimolar. The medium can also comprise a xanthine derivative, optionally at a concentration from about 0.001 millimolar to about 5.0 millimolar. The medium can be serum free. The mammalian cell line can be a hybridoma cell line or a CHO cell line.

The invention also provides a method for producing a polypeptide comprising culturing a mammalian cell line in a medium comprising a hybrid polar compound at a concentration between about 0.5 millimolar and 2.5 millimolar, an alkanoic acid at a concentration from about 0.1 millimolar and 2.0 millimolar, and a xanthine derivative at a concentration from about 0.001 millimolar to about 4 millimolar.

In still another embodiment, the invention provides a method for producing a polypeptide, optionally RANK:Fc, type II interleukin-1 receptor, TNFR:Fc, CD40 ligand, TRAIL, flt3-ligand, IL-4 receptor, G-CSF, erythropoietin, an antibody, or a substantially similar polypeptide, comprising culturing mammalian cells, which may have been genetically engineered to produce any of these polypeptides, in a medium comprising between about 0.1 millimolar and about 5 millimolar HMBA, from about 0.1 millimolar to about 2 millimolar butyric acid, and from about 0.1 millimolar to about 4 millimolar caffeine at a temperature from about 29° C. to about 36° C. or from about 30° C. to about 33° C.

DETAILED DESCRIPTION OF THE INVENTION

Figure 1:
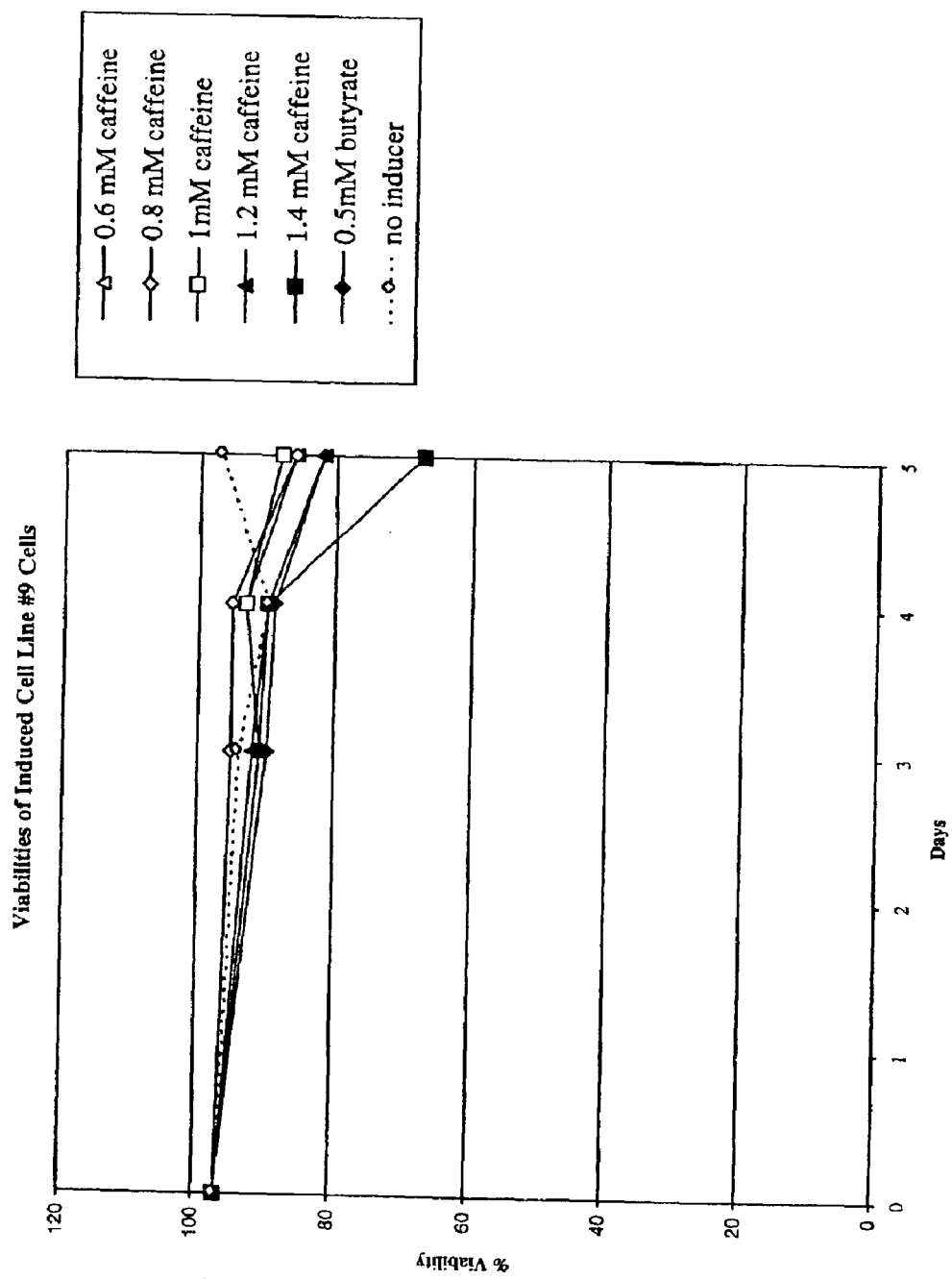
FIG. 1 shows the percentage of the total cells that are viable under the indicated conditions at 31° C. for the #9 CHO cell line as a function of days in culture.

An "antibody" is a polypeptide or complex of polypeptides, each of which comprises at least one variable antibody immunoglobulin domain and at least one constant antibody immunoglobulin domain. Antibodies may be single chain antibodies, dimeric antibodies, or some higher order complex of polypeptides including, but not limited to, heterodimeric antibodies. A "human antibody" is an antibody encoded by nucleic acids that are ultimately human in origin. Such an antibody can be expressed in a non-human cell or organism. For example, DNA encoding a human antibody can be introduced into tissue culture cells and expressed in transformed cell lines. Alternatively, human antibodies can be expressed in transgenic animals such as, for example, the transgenic mice described in Mendez et al. ((1997), Nature Genetics 16(4): 146–56). Such transgenic mice are utilized in making the fully human antibodies in U.S. Pat. No. 6,235,883 B1. Human antibodies can also be expressed in hybridoma cells. A "humanized antibody" is a chimeric antibody comprising complementarity determining regions (CDR1, CDR2, and CDR3) from a non-human source and other regions that conform to sequences in human antibodies (and may be of human origin) as explained in, e.g., U.S. Pat. Nos. 5,558,864 and 5,693,761 and International Patent Application WO 92/11018.

A "constant antibody immunoglobulin domain" is an immunoglobulin domain that is identical to or substantially similar to a $C_L$, $C_H1$, $C_H2$, $C_H3$, or $C_H4$, domain of human or animal origin. See e.g. Hasemann and Capra, Immunoglobulins: Structure and Function, in William E. Paul, ed., Fundamental Immunology, Second Edition, 209, 210–218 (1989); Kabat et al., Sequences of Proteins of Immunological Interest, U.S. Dept. of Health and Human Services (1991).

An "$F_C$ portion of an antibody" includes human or animal immunoglobulin domains $C_H2$ and $C_H3$ or immunoglobulin domains substantially similar to these. For discussion, see Hasemann and Capra, supra, at 212–213 and Kabat et al., supra.

Cells have been "genetically engineered" to express a specific polypeptide when recombinant nucleic acid sequences that allow expression of the polypeptide have been introduced into the cells using methods of "genetic engineering," such as viral infection with a recombinant virus, transfection, transformation, or electroporation. See e.g. Kaufman et al. (1990), Meth. Enzymol. 185: 487–511; Current Protocols in Molecular Biology, Ausubel et al., eds. (Wiley & Sons, New York, 1988, and quarterly updates). Infection with an unaltered, naturally-occurring virus, such as, for example, hepatitis B virus, human immunodeficiency virus, adenovirus, etc., does not constitute genetic engineering as meant herein. The term "genetic engineering" refers to a recombinant DNA or RNA method used to create a host cell that expresses a gene at elevated levels or at lowered levels, or expresses a mutant form of the gene. In other words, the cell has been transfected, transformed or transduced with a recombinant polynucleotide molecule, and thereby altered so as to cause the cell to alter expression of a desired polypeptide. For the purposes of the invention, the antibodies produced by a hybridoma cell line resulting from a cell fusion are not "recombinant polypeptides." Further, viral polypeptides produced by a cell as a result of viral infection are also not "recombinant polypeptides" as meant herein unless the viral nucleic acid has been altered by genetic engineering prior to infecting the cell. The methods of "genetic engineering" also encompass numerous methods including, but not limited to, amplifying nucleic acids using polymerase chain reaction, assembling recombinant DNA molecules by cloning them in *Escherichia coli*, restriction enzyme digestion of nucleic acids, ligation of nucleic acids, and transfer of bases to the ends of nucleic acids, among numerous other methods that are well-known in the art. See e.g. Sambrook et al., Molecular Cloning: A Laboratory Manual, $2^{nd}$ ed., vol. 1–3, Cold Spring Harbor Laboratory, 1989. Methods and vectors for genetically engineering cells and/or cell lines to express a polypeptide of interest are well known to those skilled in the art. Genetic engineering techniques include but are not limited to expression vectors, targeted homologous recombination and gene activation (see, for example, U.S. Pat. No. 5,272,071 to Chappel) and trans activation by engineered transcription factors (see e.g., Segal et al., 1999, Proc. Natl. Acad. Sci. USA 96(6) :2758–63). Optionally, the polypeptides are expressed under the control of a heterologous control element such as, for example, a promoter that does not in nature direct the production of that polypeptide. For example, the promoter can be a strong viral promoter (e.g., CMV, SV40) that directs the expression of a mammalian polypeptide. The host cell may or may not normally produce the polypeptide. For example, the host cell can be a CHO cell that has been genetically engineered to produce a human polypeptide, meaning that nucleic acid encoding the human polypeptide has been introduced into the CHO cell. Alternatively, the host cell can be a human cell that has been genetically engineered to produce increased levels of a human polypeptide normally present only at very low levels (e.g., by replacing the endogenous promoter with a strong viral promoter).

"Growth phase" means a period during which cultured cells are rapidly dividing and increasing in number. During growth phase, cells are generally cultured in a medium and under conditions designed to maximize cell proliferation.

A "hybrid polar compound" is compound having two polar groups separated by an apolar carbon chain. This includes hexamethylene bisacetamide (HMBA) and the other molecules discussed below and in the following references: Richon et al. (1998), Proc. Natl. Acad. Sci. 95: 3003–07; Marks et al. (1994), Proc. Natl. Acad. Sci. 91: 10251–54; and U.S. Pat. Nos. 5,055,608 and 6,087,367.

The production of a polypeptide is "increased" by the addition of an inducing agent, such as hexamethylene bisacetamide (HMBA) or caffeine, if the amount the polypeptide produced in a culture containing the inducing agent is more than the amount of the polypeptide produced in an otherwise identical culture that does not contain the inducing agent. Similarly, the production of a polypeptide is "increased" by growth at a temperature other than 37° C. if the amount of polypeptide produced in a culture incubated at a temperature other than 37° C. is more than the amount of the polypeptide produced in an otherwise identical culture incubated at 37° C.

A "multimerization domain" is a domain within a polypeptide molecule that confers upon it a propensity to associate with other polypeptide molecules through covalent or non-covalent interactions.

A "naturally-occurring polypeptide" is a polypeptide that occurs in nature, that is, a polypeptide that can be produced by cells that have not been genetically engineered. Such a polypeptide may also be produced by cells genetically engineered to produce it.

"Polypeptide" means a chain of at least 6 amino acids linked by peptide bonds. Optionally, a polypeptide can comprise at least 10, 20, 30, 40, 50, 60, 70, 80, 90, 100, 150, 200, 250, or 300 amino acids linked by peptide bonds.

"Production medium" means a cell culture medium designed to be used to culture cells during a production phase.

"Production phase" means a period during which cells are producing maximal amounts of recombinant polypeptide. A production phase is characterized by less cell division than during a growth phase and by the use of medium and culture conditions designed to maximize polypeptide production.

A "recombinant fusion polypeptide" is a fusion of all or part of at least two polypeptides, which is made using the methods of genetic engineering.

A "recombinant polypeptide" is a polypeptide resulting from the process of genetic engineering. For the purposes of the invention, the antibodies produced by a hybridoma cell line resulting from a cell fusion are not "recombinant polypeptides." Further, viral proteins produced by a cell as a result of viral infection with a naturally-occurring virus are also not "recombinant polypeptides" as meant herein unless the viral nucleic acid has been altered by genetic engineering prior to infecting the cell.

"Substantially similar" polypeptides are at least 80%, optionally at least 90%, identical to each other in amino acid sequence and maintain or alter in a desirable manner the biological activity of the unaltered polypeptide. Conservative amino acid substitutions, unlikely to affect biological activity, include, without limitation, the following: Ala for Ser, Val for Ile, Asp for Glu, Thr for Ser, Ala for Gly, Ala for Thr, Ser for Asn, Ala for Val, Ser for Gly, Tyr for Phe, Ala for Pro, Lys for Arg, Asp for Asn, Leu for Ile, Leu for Val, Ala for Glu, Asp for Gly, and these changes in the reverse. See e.g. Neurath et al., *The Proteins*, Academic Press, New York (1979). In addition exchanges of amino acids among members of the following six groups of amino acids will be considered to be conservative substitutions for the purposes of the invention. The groups are: 1) methionine, alanine, valine, leucine, and isoleucine; 2) cysteine, serine, threonine, asparagine, and glulamine; 3) aspartate and glutamate; 4) histidine, lysine, and arginine; 5) glycine and proline; and 6) tryptophan, tyrosine, and phenylalanine. The percent identity of two amino sequences can be determined by visual inspection and mathematical calculation, or more preferably, the comparison is done by comparing sequence information using a computer program such as the Genetics Computer Group (GCG; Madison, Wis.) Wisconsin package version 10.0 program, 'GAP' (Devereux et al. (1984), *Nucl. Acids Res.* 12: 387) or other comparable computer programs. The preferred default parameters for the 'GAP' program includes: (1) the weighted amino acid comparison matrix of Gribskov and Burgess (1986), *Nucl. Acids Res.* 14: 6745, as described by Schwartz and Dayhoff, eds., *Atlas of Polypeptide Sequence and Structure*, National Biomedical Research Foundation, pp. 353–358 (1979), or other comparable comparison matrices; (2) a penalty of 30 for each gap and an additional penalty of 1 for each symbol in each gap for amino acid sequences; (3) no penalty for end gaps; and (4) no maximum penalty for long gaps. Other programs used by those skilled in the art of sequence comparison can also be used.

"Transition phase" means a period of cell culture between a "growth phase" and a "production phase." During transition phase, the medium and environmental conditions are typically shifted from those designed to maximize proliferation to those designed to maximize polypeptide production.

A "variable antibody immunoglobulin domain" is an immunoglobulin domain that is identical or substantially similar to a $V_L$ or a $V_H$ domain of human or animal origin.

The present invention is directed towards improved methods for culturing mammalian cells, which may have been genetically engineered to produce a particular polypeptide. In particular, the invention is directed towards culture methods that maximize the production of specific polypeptides. It is also directed towards methods of producing and obtaining such polypeptides from cultured mammalian cells. Polypeptides are useful in a large variety of diagnostic, therapeutic, agricultural, nutritional, and research applications.

As shown by the experimental data reported herein, it has been discovered that xanthine derivatives and hybrid polar compounds used separately or together can dramatically induce the production of recombinant polypeptide from CHO cell lines. In particular, addition of the xanthine derivative caffeine to the production phase of a cell culture enhances recombinant polypeptide production. The hybrid polar compound hexamethylene bisacetamide is also shown to be an effective inducer of recombinant polypeptide production. Further, other inducers, such as, for example, alkanoic acids, can also be added to either a xanthine derivative, a hybrid polar compound, or both. Other methods, such as, for example, culturing the cells at temperatures from about 29° C. to about 36° C., between about 29° C. and 35° C., and/or from about 30° C. to about 33° C. can also be used. Thus, the invention relates to inducing increased production of a recombinant polypeptide from a cell grown in culture by exposing the cell to chemical inducers, including hybrid polar compounds and/or xanthine derivatives.

The methods of the invention include culturing mammalian cells in medium comprising a hybrid polar compound, for example, hexamethylene bisacetamide (HMBA), optionally at temperatures between about 29° C. and 35° C. or from about 30° C. to about 33° C. Other embodiments of the invention encompass culture conditions in which an alkanoic acid and/or a xanthine, in addition to the hybrid polar compound, are added to the culture medium. In one embodiment, a xanthine and a hybrid polar compound and culture temperatures between about 29° C. and 36° C. are used. Another embodiment comprises the addition of an alkanoic acid and a hybrid polar compound plus culture temperatures between about 29° C. and 36° C. Still another embodiment comprises addition of a xanthine, an alkanoic acid, and a hybrid polar compound plus culture temperatures between about 29° C. and 36° C. Optionally, cell culture using the methods of the invention can take place during a production phase, as distinguished from a growth phase. A growth phase can be distinguished from a production phase by, for example, a temperature shift and/or a change in medium such as, for example, the addition of one or more inducers.

In one aspect, the invention provides a method comprising growing in culture a mammalian cell that has been genetically engineered to produce a polypeptide; and adding to the culture a xanthine derivative. A genetically engineered cell may be a cell that has been transformed with a recombinant vector encoding the polypeptide. In addition, the polypeptide can be expressed under the control of a heterologous promoter such as, for example, a CMV promoter. Typically, the cell does not naturally express the polypeptide or only naturally expresses the polypeptide at very low levels (in the absence of genetic engineering). In another aspect, the invention provides a culture containing a cell genetically engineered to produce a polypeptide, a production medium, and the xanthine derivative.

In addition, the methods and compositions of the invention can be used in combination with any other known or yet to be discovered methods of inducing the production of recombinant polypeptides. Such techniques include cold temperature shift, alkanoic acid additions (as described in U.S. Pat. No. 5,705,364 to Etcheverry et al., incorporated herein by reference), DMF, and DMSO, to name just a few examples, as well as any yet to be described and/or discovered induction techniques. As used herein, "inducing" polypeptide production or "induction" refers to culturing cells under a set of conditions designed to maximize the total amount of a desired polypeptide made by the cells. An "inducer" is an agent that, when added to culture medium, can increase the production of a desired polypeptide in at least some cell lines. Combining the addition of xanthine derivatives with other protein induction techniques can have a synergistic effect on polypeptide induction, allowing for lower additions of xanthine derivatives and/or lower additions of other inducing agents and/or more conservative temperature shifts. The other methods of induction can take place at around the same time as xanthine addition, and/or before and/or after xanthine addition. For example, one can shift the temperature of the culture at day 0, and then add a xanthine derivative and/or a hybrid polar compound, and optionally other chemical inducers, later, e.g. one to several hours or days later. Such a protocol allows some additional growth of a seeded culture before full induction. Furthermore, multiple additions of xanthine derivatives and/or hybrid polar compounds can be added to the culture during the production phase, separated by about 12, 24, 48, and/or 72 hours or more, with or without additions of other inducing agents or changes in culture conditions. For example, an inducer can be added at day 0 and again at day 4. Alternatively, an inducer can be added for the first time one, two, three, or four days after a temperature shift.

In one aspect, the invention entails performing a low temperature shift (shifting the temperature of the medium from the optimal growth temperature, usually around 37° C., to a lower temperature, usually from about 29° C. to about 36° C., and optionally about 30° C. to about 34° C. at the time of, before, and/or after adding the xanthine derivative or the hybrid polar compound. Alternatively, or in addition, an alkanoic acid or salt thereof (e.g. sodium butyrate) can be added to the culture at around the same time as the xanthine derivative and/or hybrid polar compound is added. Alkanoic acid can be added at concentrations typically used for induction, or even at lower concentrations than would typically be used. Thus, by manipulating both transcriptional and post-transcriptional controls, higher levels of productivity may be achieved.

There are individual differences between cell lines in the effectiveness of various inducers. For example, although sodium butyrate is a widely-used inducer, it can have no effect or an adverse effect on polypeptide production in some cell lines. See Table 5. Different inducers or different concentrations of the same inducers may be appropriate for different cell lines. Furthermore, different temperatures may be appropriate for different cell lines. In spite of this variability, some inducers, such as, for example, caffeine, hexamethylene bisacetamide, and sodium butyrate, can be useful in a wide variety, though perhaps not all, cell lines.

Generally, xanthine derivatives have the structure illustrated below.

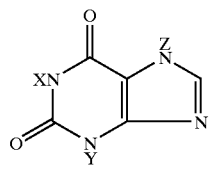

X, Y, and Z can be independently selected from a straight or branched chain alkyl radical having from 1 to 12 carbons, a straight or branched chain alkynyl radical having from 1 to 12 carbons (including a propynyl radical), a straight or branched chain acyl radical having from 1 to 12 carbons, a straight or branched chain radical with the structure —R-acyl containing from 1 to 12 carbons where R is a saturated or unsaturated aliphatic group, a straight or branched chain allenyl radical having from 1 to 12 carbons, a straight or branched chain hydroxyalkyl radical having from 1 to 12 carbons, a straight or branched chain hydroxyallenyl radical having from 1 to 12 carbons, a straight or branched chain radical with the structure -allenyl-halogen having from 1 to 12 carbons, a cyclohexyl radical, and hydrogen. In some embodiments, at least one of X, Y and Z is a methyl group. In some embodiments, each of X and Y independently represents a hydrogen atom, a linear or branched alkyl radical having up to 5 carbon atoms, an allyl radical, a propynyl radical or a cyclohexyl radical, with the proviso that X and Y do not simultaneously represent a hydrogen atom, and Z represents a hydrogen, methyl, ethyl, hydroxymethyl, hydroxyethyl or heterocyclo radical. These xanthines can be obtained using conventional processes and/or purchased. A number of different xanthine derivatives that can be used are described in Beavo et al. (1970), Molec. Pharm. 6:597–603, and incorporated by reference herein.

Illustrative examples of xanthine derivatives that can be used in the methods and compositions of the invention include, but are not limited to, caffeine (1,3,7-trimethylxanthine), theophylline (1,3-dimethylxanthine), theobromine (3,7-dimethylxanthine), 3-isobutyl-1-methylxanthine, 3-butyl-1-methylxanthine, 1,3,7-triethylxanthine, 3-cyclohexyl-1-ethylxanthine, 3-ethyl-1-propynylxanthine, 3-ethyl-1-pentylxanthine, pentoxifylline, and aminophylline. Aminophylline is theophylline compound with 1,2-ethylenediamine (2:1) dihydrate. Generally, the xanthine derivative is added at a concentration in the culture from about 0.0005 to about 25 millimolar, optionally from about 0.001 to about 10 millimolar, from about 0.005 to about 5 millimolar, or from about 0.01 to about 3 millimolar. The optimal concentration of the xanthine derivative will vary depending upon its activity and the cell line, and can be determined by those skilled in the art using the guidance provided herein.

The xanthine derivative can be dissolved in any appropriate solvent. For example, 3-isobutyl-1-methylxanthine (IBX) can be dissolved in water, but must to be heated to almost the boiling point. Alternatively, IBX can be dissolved in the solvents DMSO (dimethylsulfoxide), DMF (dimethylformamide), or DMA (dimethylacetamide). IBX can also be easily dissolved as a 100 millimolar stock solution in 0.5 M NaOH. Dilutions of this stock solution can be added to the induction media as it is being prepared (pre-sterile) and the effects of the NaOH should be inconsequential since base must often be added to raise the pH of the medium to 7.0.

Many of the xanthine derivatives for use in the invention are cAMP phosphodiesterase inhibitors. Thus, in addition to using xanthine derivatives that are cAMP phosphediesterase inhibitors, it is believed that cAMP phosphodiesterase inhibitors that are not xanthine derivatives could also be used to induce polypeptide production in alternative methods of the invention. Examples of such inducers include but are not limited to imidazopyrimidine, pyrazolopyridine, etazolate, pyrazoloquinoline, and triazoloquinazoline (Pflugers Archiv 407: S31, 1986). Other examples cAMP phosphodiesterase inhibitors can be found in U.S. Pat. No. RE37,234, which is incorporated by reference herein.

The hybrid polar compounds, the use of which is encompassed by the invention, can have two polar groups separated by a non-polar carbon chain, such as those described in Richon et al. (1998), Proc. Natl. Acad. Sci. 95: 3003–07, Marks et al. (1994), Proc. Natl. Acad. Sci. 91: 10251–54, U.S. Pat. Nos. 5,055,608 and 6,087,367. The hybrid polar compounds of the invention may have the property of inducing one or more changes characteristic of a terminally differentiated state of the host cells. These compounds include those with the structure:

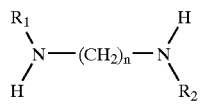

$R_1$ and $R_2$ can be the same as or different from each other. $R_1$ and $R_2$ can each be a carbonyl group to which a hydrogen atom, a hydroxyl group, a substituted or unsubstituted, branched or unbranched alkyl, alkenyl, cycloalkyl, aryl, alkynl, allenyl, allyl, alkyloxy, aryloxy, arylalkyloxy, which contains 12 or fewer carbon atoms, or pyridine group, may also be attached. The "n" can be an integer from about four to about eight. Specifically, HMBA is included within this class of hybrid polar compounds, and its structure is:

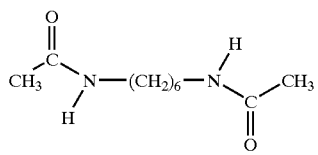

The present invention further encompasses the use of hybrid polar compounds with the following structure:

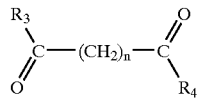

$R_3$ and $R_4$ can be the same as or different from each other. When $R_3$ and $R_4$ are the same, each is a substituted or unsubstituted arylamino, cycloalkylamino, pyridineamino, piperidino, 9-purine-6-amine, or thiozoleamino group containing 12 or fewer carbon atoms. Where $R_3$ and $R_4$ are different, $R_3$ is equal to $R_5$—N—$R_6$, where $R_5$ and $R_6$ are the same as or different from each other and are a hydrogen atom, a hydroxyl group, a substituted or unsubstituted, branched or unbranched alkyl, alkenyl, cycloalkyl, aryl, alkynl, allenyl, allyl, alkyloxy, aryloxy, arylalkyloxy, or pyridine group, which contains 12 or fewer carbon atoms, or $R_5$ and $R_6$ bond together to form a piperidine group, and $R_4$ is a hydroxylamino, hydroxyl, amino, alkylamino, dialkylamino, or alkyloxy group, which contains 12 or fewer carbon atoms. The "n" is an integer from about four to about eight.

The invention further embraces the use of all compounds disclosed in U.S. Pat. No. 6,087,367, U.S. Pat. No. 5,055,608, Richon et al., supra, and Marks et al., supra. In some of these, the apolar carbon chain may be shorter than 4 carbons and longer than 8 carbons, and it may be interrupted by aromatic groups, apolar groups, and/or polar groups.

If HMBA is used, it can be added at concentrations from about 0.1 millimolar to about 20 millimolar, optionally, between about 0.1 millimolar and about 5 millimolar. Other hybrid polar compounds may be active at lower or higher concentrations. The optimal concentration for a particular hybrid polar compound will vary depending on its activity and the cell line in which it is used and can be determined by one of skill in the art using routine methods and the guidance provided herein. For example, compounds such as suberoylanilide hydroxamic acid or m-carboxycinnamic acid bishydroxamide can be used at concentrations about one thousand fold lower than those required for HMBA, from about 0.01 micromolar to about 10 micromolar. See Richon et al., supra. Concentrations of hybrid polar compounds required to induce cell differentiation as disclosed in Marks et al. (supra) and Richon et al. (supra) can be used as a guide for determining the concentration of a hybrid polar compound required to enhance polypeptide production. Determination of the concentration needed for a specific hybrid polar compound used in a specific cell line can be done using routine methods as described herein and the guidance provided in Richon et al. (supra) and Marks et al. (supra).

The alkanoic acids for use in the invention include the selected acid and/or a corresponding salt. The acids include straight or branched chain, saturated or unsaturated alkanoic acids or salts thereof. An alkanoic acid generally comprises from one to ten carbon atoms. Examples of alkanoic acids contemplated by the invention are pentanoic acid, butyric acid, isobutyric acid, propionic acid, and acetic acid. Concentrations for alkanoic acids encompassed by the invention range from about 0.05 millimolar to about 10 millimolar, optionally from about 0.1 millimolar to about 2 millimolar. Appropriate concentrations of alkanoic acids will vary depending upon their activity and the cell line and can be determined by one of skill in the art using routine methods and the guidance provided herein. An exemplary salt of butyric acid is sodium butyrate. Appropriate salts of the alkanoic acids described above include those comprising sodium, potassium, or ammonium groups, among others.

Particularly preferred polypeptides for expression are polypeptide-based drugs, also known as biologics. Preferably, the polypeptides are secreted as extracellular products. The polypeptide being produced can comprise part or all of a polypeptide that is identical or substantially similar to a naturally-occurring polypeptide, and/or it may, or may not, be a recombinant fusion polypeptide. Optionally, the polypeptide may be a human polypeptide, a fragment thereof, or a substantially similar polypeptide that is at least 15 amino acids in length. It may comprise a non-antibody polypeptide and/or an antibody. It may be produced intracellularly or be secreted into the culture medium from which it can be recovered. It may or may not be a soluble polypeptide.

The polypeptide being produced can comprise part or all of a polypeptide that is identical or substantially similar to a naturally-occurring polypeptide, and/or it may, or may not, be a recombinant fusion polypeptide. It may comprise a non-antibody polypeptide and/or an antibody. It may be produced intracellularly or be secreted into the culture medium from which it can be recovered.

The invention can be used to induce the production of just about any polypeptide, and is particularly advantageous for polypeptides whose expression is under the control of a strong promoter, such as for example, a viral promoter, and/or polypeptides that are encoded on a message that has an adenoviral tripartite leader element. Examples of useful expression vectors that can be used to produce proteins are disclosed in International Application WO 01/27299 and in McMahan et al., (1991), EMBO J. 10: 2821, which describes the pDC409 vector. A protein is generally understood to be a polypeptide of at least about 10 amino acids, optionally about 25, 75, or 100 amino acids.

Generally, the methods of the invention arc useful for inducing the production of recombinant polypeptides. Some polypeptides that can be produced with the methods of the invention include polypeptides comprising amino acid sequences identical to or substantially similar to all or part of one of the following polypeptides: a flt3 ligand (as described in International Application WO 94/28391, incorporated herein by reference), a CD40 ligand (as described in U.S. Pat. No. 6,087,329 incorporated herein by reference), erythropoeitin, thrombopoeitin, calcitonin, leptin, IL-2, angiopoietin-2 (as described by Maisonpierre et al. (1997), Science 277(5322): 55–60, incorporated herein by reference), Fas ligand, ligand for receptor activator of NF-kappa B (RANKL, as described in International Application WO 01/36637, incorporated herein by reference), tumor necrosis factor (TNF)-related apoptosis-inducing ligand (TRAIL, as described in International Application WO 97/01633, incorporated herein by reference), thymic stroma-derived lymphopoietin, granulocyte colony stimulating factor, granulocyte-macrophage colony stimulating factor (GM-CSF, as described in Australian Patent No. 588819, incorporated herein by reference), mast cell growth factor, stem cell growth factor (described in e.g. U.S. Pat. No. 6,204,363, incorporated herein by reference), epidermal growth factor, keratinocyte growth factor, megakaryote growth and development factor, RANTES, growth hormone, insulin, insulinotropin, insulin-like growth factors, parathyroid hormone, interferons including α interferons, γ interferon, and consensus interferons (such as those described in U.S. Pat. Nos. 4,695,623 and 4,897471, both of which are incorporated herein by reference), nerve growth factor, brain-derived neurotrophic factor, synaptotagmin-like proteins (SLP 1–5), neurotrophin-3, glucagon, interleukins 1 through 18, colony stimulating factors, lymphotoxin-β, tumor necrosis factor (TNF), leukemia inhibitory factor, oncostatin-M, and various ligands for cell surface molecules ELK and Hek (such as the ligands for eph-related kinases or LERKS). Descriptions of polypeptides that can be produced according to the inventive methods may be found in, for example, *Human Cytokines: Handbook for Basic and Clinical Research. Vol. II* (Aggarwal and Gutterman, eds. Blackwell Sciences, Cambridge, Mass., 1998); *Growth Factors: A Practical Approach* (McKay and Leigh, eds., Oxford University Press Inc., New York, 1993); and *The Cytokine Handbook* (A. W. Thompson, ed., Academic Press, San Diego, Calif., 1991), all of which are incorporated herein by reference.

Other polypeptides that can be produced using the methods of the invention include polypeptides comprising all or part of the amino acid sequence of a receptor for any of the above-mentioned polypeptides, an antagonist to such a receptor or any of the above-mentioned polypeptides, and/or polypeptides substantially similar to such receptors or antagonists. These receptors and antagonists include: both forms of tumor necrosis factor receptor (TNFR, referred to as p55 and p75, as described in U.S. Pat. No. 5,395,760 and U.S. Pat. No. 5,610,279, both of which are incorporated herein by reference), Interleukin-1 (IL-1) receptors (types I and II; described in EP Patent No. 0 460 846, U.S. Pat. No. 4,968,607, and U.S. Pat. No. 5,767,064, all of which are incorporated herein by reference), IL-1 receptor antagonists (such as those described in U.S. Pat. No. 6,337,072, incorporated herein by reference), IL-1 antagonists or inhibitors (such as those described in U.S. Pat. Nos. 5,981,713, 6,096,728, and 5,075,222, all of which are incorporated herein by reference) IL-2 receptors, IL-4 receptors (as described in EP Patent No. 0 367 566 and U.S. Pat. No. 5,856,296, both of which are incorporated by reference), IL-15 receptors, IL-17 receptors, IL-18 receptors, granulocyte-macrophage colony stimulating factor receptor, granulocyte colony stimulating factor receptor, receptors for oncostatin-M and leukemia inhibitory factor, receptor activator of NF-kappa B (RANK, described in WO 01/36637 and U.S. Pat. No. 6,271,349, both of which are incorporated by reference), osteoprotegerin (described in e.g. U.S. Pat. No. 6,015,938, incorporated by reference), receptors for TRAIL (including TRAIL receptors 1, 2, 3, and 4), and receptors that comprise death domains, such as Fas or Apoptosis-Inducing Receptor (AIR).

Other polypeptides that can be produced using the process of the invention include polypeptides comprising all or part of the amino acid sequences of differentiation antigens (referred to as CD polypeptides) or their ligands or polypeptides substantially similar to either of these. Such antigens are disclosed in *Leukocyte Typing VI* (*Proceedings of the VIth International Workshop and Conference*, Kishimoto, Kikutani et al., eds., Kobe, Japan, 1996, which is incorporated by reference). Similar CD polypeptides are disclosed in subsequent workshops. Examples of such antigens include CD22, CD27, CD30, CD39, CD40, and ligands thereto (CD27 ligand, CD30 ligand, etc.). Several of the CD antigens are members of the TNF receptor family, which also includes 41BB and OX40. The ligands are often members of the TNF family, as are 41BB ligand and OX40 ligand. Accordingly, members of the TNF and TNFR families can also be purified using the present invention.

Enzymatically active polypeptides or their ligands can also be produced according to the methods of the invention. Examples include polypeptides comprising all or part of one of the following polypeptides or their ligands or a polypeptide substantially similar to one of these: metalloproteinase-disintegrin family members, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, TNF-alpha Converting Enzyme, ligands for any of the above-mentioned enzymes, and numerous other enzymes and their ligands.

The methods of the invention can also be used to produce antibodies or portions thereof and chimeric antibodies, i.e. antibodies having human constant antibody immunoglobulin domains coupled to one or more murine variable antibody immunoglobulin domain, fragments thereof, or substantially similar proteins. The method of the invention may also be used to produce conjugates comprising an antibody and a cytotoxic or luminescent substance. Such substances include: maytansine derivatives (such as DM1); enterotoxins (such as a Staphlyococcal enterotoxin); iodine isotopes (such as iodine-125); technium isotopes (such as Tc-99m); cyanine fluorochromes (such as Cy5.5.18); and ribosome-inactivating polypeptides (such as bouganin, gelonin, or saporin-S6). The invention can also be used to produce chimeric proteins selected in vitro to bind to a specific target protein and modify its activity such as those described in International Applications WO 01/83525 and WO 00/24782, both of which are incorporated by reference. Examples of antibodies, in vitro-selected chimeric proteins, or antibody/cytotoxin or antibody/luminophore conjugates that can be produced by the methods of the invention include those that recognize any one or a combination of polypeptides including, but not limited to, the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1α, IL-1β, IL-2, IL-3, IL-7, IL-4, IL-5, IL-8, IL-10, IL-2 receptor, IL-4 receptor, IL-6 receptor, IL-13 receptor, IL-18 receptor subunits, PDGF-β and analogs thereof (such as those described in U.S. Pat. Nos. 5,272,064 and 5,149,792), VEGF, TGF, TGF-β2, TGF-β1, EGF receptor (including those described in U.S. Pat. No. 6,235,883 B1, incorporated by reference) VEGF receptor, hepatocyte growth factor, osteoprotegerin ligand, interferon gamma, B lymphocyte stimulator (BlyS, also known as BAFF, THANK, TALL-1, and zTNF4; see Do and Chen-Kiang (2002), Cytokine Growth Factor Rev. 13(1): 19–25), C5 complement, IgE, tumor antigen CA125, tumor antigen MUC1, PEM antigen, LCG (which is a gene product that is expressed in association with lung cancer), HER-2, a tumor-associated glycoprotein TAG-72, the SK-1 antigen, tumor-associated epitopes that are present in elevated levels in the sera of patients with colon and/or pancreatic cancer, cancer-associated epitopes or polypeptides expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, L-selectin, Respiratory Syncitial Virus, human immunodeficiency virus (HIV), hepatitis B virus (HBV), *Streptococcus mutans*, and *Staphlycoccus aureus*.

The invention may also be used to produce all or part of an anti-idiotypic antibody or a substantially similar polypeptide, including anti-idiotypic antibodies against: an antibody targeted to the tumor antigen gp72; an antibody against the ganglioside GD3; an antibody against the ganglioside GD2; or antibodies substantially similar to these.

The methods of the invention can also be used to produce recombinant fusion polypeptides comprising any of the above-mentioned polypeptides. For example, recombinant fusion polypeptides comprising one of the above-mentioned polypeptides plus a multimerization domain, such as a leucine zipper, a coiled coil, an Fc portion of an antibody, or a substantially similar protein, can be produced using the methods of the invention. See e.g. WO94/10308; Lovejoy et al. (1993), Science 259: 1288–1293; Harbury et al. (1993), Science 262: 1401–05; Harbury et al. (1994), Nature 371:80–83; Håkansson et al. (1999), Structure 7:255–64, all of which are incorporated by reference. Specifically included among such recombinant fusion polypeptides are polypeptides in which a portion of TNFR or RANK is fused to an Fc portion of an antibody (TNFR:Fc or RANK:Fc). TNFR:Fc comprises the Fc portion of an antibody fused to an extracellular domain of TNFR, which includes amino acid sequences substantially similar to amino acids 1–163, 1–185, or 1–235 of FIG. 2A of U.S. Pat. No. 5,395,760, which is incorporated by reference. RANK:Fc is described in International Application WO 01/36637, which is incorporated by reference.

Preferably, the polypeptides are expressed under the control of a heterologous control element such as, for example, a promoter that does not in nature direct the production of that polypeptide. For example, the promoter can be a strong viral promoter (e.g., CMV, SV40) that directs the expression of a mammalian polypeptide. The host cell may or may not normally produce the polypeptide. For example, the host cell can be a CHO cell that has been genetically engineered to produce a human polypeptide, meaning that nucleic acid encoding the human polypeptide has been introduced into the CHO cell. Alternatively, the host cell can be a human cell that has been genetically engineered to produce increased levels of a human polypeptide normally present only at very low levels (e.g., by replacing the endogenous promoter with a strong viral promoter). For the production of recombinant polypeptides, an expression vector encoding the recombinant polypeptide can be transferred, for example by transfection or viral infection, into a substantially homogeneous culture of host cells. The expression vector, which can be constructed using the methods of genetic engineering, can include nucleic acids encoding the polypeptide of interest operably linked to suitable regulatory sequences.

The regulatory sequences are typically derived from mammalian, microbial, viral, and/or insect genes. Examples of regulatory sequences include transcriptional promoters, operators, and enhancers, a ribosomal binding site (see e.g. Kozak (1991), J. Biol. Chem. 266:19867–19870), appropriate sequences to control transcriptional and translational initiation and termination, polyadenylation signals (see e.g. McLauchlan et al. (1988), Nucleic Acids Res. 16:5323–33), and matrix and scaffold attachment sites (see Phi-Van et al. (1988), Mol. Cell. Biol. 10:2302–07; Stief et al. (1989), Nature 341:342–35; Bonifer et al. (1990), EMBO J. 9:2843–38). Nucleotide sequences are operably linked when the regulatory sequence functionally relates to the polypeptide coding sequence. Thus, a promoter nucleotide sequence is operably linked to a polypeptide coding sequence if the promoter nucleotide sequence controls the transcription of the coding sequence. A gene encoding a selectable marker is generally incorporated into the expression vector to facilitate the identification of recombinant cells.

Transcriptional and translational control sequences for mammalian host cell expression vectors can be excised from viral genomes. Commonly used promoter and enhancer sequences are derived from polyoma virus, adenovirus 2, simian virus 40 (SV40), and human cytomegalovirus (CMV). For example, the human CMV promoter/enhancer of immediate early gene 1 may be used. See e.g. Patterson et al. (1994), Applied Microbiol. Biotechnol. 40:691–98. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al. (1978), Nature 273:113; Kaufman (1990), Meth. in Enzymol. 185:487–511). Smaller or larger SV40 fragments can also be used, provided the approximately 250 bp sequence extending from the Hind III site toward the Bgl I site located in the SV40 viral origin of replication site is included.

In addition, a sequence encoding an appropriate native or heterologous signal peptide (leader sequence) can be incorporated into the expression vector, to promote extracellular secretion of the recombinant polypeptide. The signal peptide will be cleaved from the recombinant polypeptide upon secretion from the cell. The choice of signal peptide or leader depends on the type of host cells in which the recombinant polypeptide is to be produced. Examples of signal peptides that are functional in mammalian host cells include the signal sequence for interleukin-7 (IL-7) described in U.S. Pat. No. 4,965,195, the signal sequence for interleukin-2 receptor described in Cosman et al. (1984), Nature 312:768; the interleukin-4 receptor signal peptide described in EP Patent No. 367,566; the type I interleukin-1 receptor signal peptide described in U.S. Pat. No. 4,968,607; and the type II interleukin-1 receptor signal peptide described in EP Patent No. 0 460 846.

Established methods for introducing DNA into mammalian cells have been described. Kaufman, R. J., *Large Scale Mammalian Cell Culture*, 1990, pp. 15–69. Additional protocols using commercially available reagents, such as the cationic lipid reagents LIPOFECTAMINE™, LIPOFECTAMINE™-2000, or LIPOFECTAMINE™-PLUS (which can he purchased from Invitrogen), can be used to transfect cells. Feigner et al. (1987)., Proc. Natl. Acad. Sci. USA 84:7413–7417. In addition, electroporation or bombardment with microprojectiles coated with nucleic acids can be used to transfect mammalian cells using procedures, such as those in Sambrook et al., *Molecular Cloning: A Laboratory Manual*, 2nd ed. Vol. 1–3, Cold Spring Harbor Laboratory Press (1989) and Fitzpatrick-McElligott (1992), Biotechnology (NY) 10(9): 1036–40. Selection of stable transformants can be performed using methods known in the art, such as, for example, resistance to cytotoxic drugs. Kaufman et al. ((1990), Meth. in Enzymology 185:487–511), describes several selection schemes, such as dihydrofolate reductase (DHFR) resistance. A suitable host strain for DHFR selection can be CHO strain DX-B11, which is deficient in DHFR. Urlaub and Chasin (1980), Proc. Natl. Acad. Sci. USA 77:4216–4220. A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Additional control sequences shown to improve expression of heterologous genes from mammalian expression vectors include such elements as the expression augmenting sequence element (EASE) derived from CHO cells (Morris et al., in *Animal Cell Technology*, pp. 529–534 (1997); U.S. Pat. Nos. 6,312,951 B1, 6,027,915, and 6,309,841 B1) and the tripartite leader (TPL) and VA gene RNAs from Adenovirus 2 (Gingeras et al. (1 982), *J. Biol. Chem.* 257:13475–13491). The internal ribosome entry site (IRES) sequences of viral origin allows dicistronic mRNAs to be translated efficiently (Oh and Sarnow (1993), *Current Opinion in Genetics and Development* 3:295–300; Ramesh et al. (1996), *Nucleic Acids Research* 24:2697–2700). Expression of a heterologous cDNA as part of a dicistronic mRNA followed by the gene for a selectable marker (e.g. DHFR) has been shown to improve transfectability of the host and expression of the heterologous cDNA (Kaufman et al. (1990), Methods in Enzymol. 185:487–511). Exemplary expression vectors that employ dicistronic mRNAs are pTR-DC/GFP described by Mosser et al., *Biotechniques* 22:150–161 (1997), and p2A5I described by Morris et al., in *Animal Cell Technology*, pp. 529–534 (1997).

A useful high expression vector, pCAVNOT, has been described by Mosley et al. ((1989), *Cell* 59:335–348). Other expression vectors for use in mammalian host cells can be constructed as disclosed by Okayama and Berg ((1983), Mol. Cell. Biol. 3:280). A useful system for stable high level expression of mammalian cDNAs in C127 murine mammary epithelial cells can be constructed substantially as described by Cosman et al. ((1986), Mol. Immunol. 23:935). A useful high expression vector, PMLSV N1/N4, described by Cosman et al. ((1984), Nature 312:768), has been deposited as ATCC 39890. Additional useful mammalian expression vectors are described in EP Patent No.-A-0 367 566 and WO 01/27299 A1. The vectors can be derived from retroviruses. In place of the native signal sequence, a heterologous signal sequence can be added, such as one of the following sequences: the signal sequence for IL-7 described in U.S. Pat. No. 4,965,195; the signal sequence for IL-2 receptor described in Cosman et al. (Nature 312:768 (1984)); the IL-4 signal peptide described in EP Patent No. 0 367 566; the typed IL-1 receptor signal peptide described in U.S. Pat. No. 4,968,607; and the type II IL-1 receptor signal peptide described in EP Patent No. 0 460 846.

The polypeptides can be produced recombinantly in eukaryotic cells and are preferably secreted by host cells adapted to grow in cell culture. Optionally, host cells for use in the invention are preferably mammalian cells. The cells can be also genetically engineered to express a gene of interest, can be mammalian production cells adapted to grow in cell culture, and/or can be homogenous cell lines. Examples of such cells commonly used in the industry are VERO, BHK, HeLa, CV1 (including Cos), MDCK, 293, 3T3, myeloma cell lines (e.g., NSO, NS1), PC12, WI38 cells, and Chinese hamster ovary (CHO) cells, which are widely used for the production of several complex recombinant polypeptides, e.g. cytokines, clotting factors, and antibodies (Brasel et al. (1996), Blood 88:2004–2012; Kaufman et al. (1988), J.Biol Chem 263:6352–6362; McKinnon et al. (1991), J Mol Endocrinol 6:231–239; Wood et al. (1990), J. Immunol. 145:3011–3016). The dihydrofolate reductase (DHFR)-deficient mutant cell lines (Urlaub et al. (1980), Proc Natl Acad Sci USA 77: 4216–4220, which is incorporated by reference), DXB11 and DG-44, are desirable CHO host cell lines because the efficient DHFR selectable and amplifiable gene expression system allows high level recombinant polypeptide expression in these cells (Kaufman R. J. (1990), Meth Enzymol 185:537–566, which is incorporated by reference). In addition, these cells are easy to manipulate as adherent or suspension cultures and exhibit relatively good genetic stability. CHO cells and recombinant polypeptides expressed in them have been extensively characterized and have been approved for use in clinical commercial manufacturing by regulatory agencies. The methods of the invention can also be practiced using hybridoma cell lines that produce an antibody. Methods for making hybridoma lines are well known in the art. See e.g. Berzofsky et al. in Paul, ed., *Fundamental Immunology, Second Edition*, pp.315–356, at 347–350, Raven Press Ltd., New York (1989). Cell lines derived from the above-mentioned lines are also suitable for practicing the invention.

According to the present invention, a mammalian host cell is cultured under conditions that promote the production of the polypeptide of interest, which can be an antibody or a recombinant polypeptide. Basal cell culture medium formulations are well known in the art. To these basal culture medium formulations the skilled artisan will add components such as amino acids, salts, sugars, vitamins, hormones, growth factors, buffers, antibiotics, lipids, trace elements and the like, depending on the requirements of the host cells to be cultured. The culture medium may or may not contain serum and/or protein. Various tissue culture media, including serum-free and/or defined culture media, are commercially available for cell culture. Tissue culture media is defined, for purposes of the invention, as a media suitable for growth of animal cells, and preferably mammalian cells, in in vitro cell culture. Typically, tissue culture media contains a buffer, salts, energy source, amino acids, vitamins and trace essential elements. Any media capable of supporting growth of the appropriate eukaryotic cell in culture can be used; the invention is broadly applicable to eukaryotic cells in culture, particularly mammalian cells, and the choice of media is not crucial to the invention. Tissue culture media suitable for use in the invention are commercially available from, e.g., ATCC (Manassas, Va.). For example, any one or combination of the following media can be used: RPMI-1640 Medium, RPMI-1641 Medium, Dulbecco's Modified Eagle's Medium (DMEM), Minimum Essential Medium Eagle, F-12K Medium, Ham's F12 Medium, Iscove's Modified Dulbecco's Medium, McCoy's 5A Medium, Leibovitz's L-15 Medium, and serum-free media such as EX-CELL™ 300 Series (available from JRH Biosciences, Lenexa, Kans., USA), among others, which can be obtained from the American Type Culture Collection or JRH Biosciences, as well as other vendors. When defined medium that is serum-free and/or peptone-free is used, the medium is usually highly enriched for amino acids and trace elements. See, for example, U.S. Pat. Nos. 5,122,469 to Mather et al. and 5,633,162 to Keen et al.

In the methods and compositions of the invention, cells can be grown in serum-free, protein-free, growth factor-free, and/or peptone-free media. The term "serum-free" as applied to media includes any mammalian cell culture medium that does not contain serum, such as fetal bovine serum. The term "insulin-free" as applied to media includes any medium to which no exogenous insulin has been added. By exogenous is meant, in this context, other than that produced by the culturing of the cells themselves. The term "IGF-1-free" as applied to media includes any medium to which no exogenous Insulin-like growth factor-1 (IGF-1) or analog (such as, for example, LongR3, [Ala31], or [Leu24][Ala31] IGF-1 analogs available from GroPep Ltd. of Thebarton, South Australia) has been added. The term "growth-factor free" as applied to media includes any medium to which no exogenous growth factor (e.g., insulin, IGF-1) has been added. The term "protein-free" as applied to media includes medium free from exogenously added protein, such as, for example, transferrin and the protein growth factors IGF-1 and insulin. Protein-free media may or may not have peptones. The term "peptone-free" as applied to media includes any medium to which no exogenous protein hydrolysates have been added such as, for example, animal and/or plant protein hydrolysates. Eliminating peptone from media has the advantages of reducing lot to lot variability and enhancing processing such as filtration. Chemically defined media are media in which every component is defined and obtained from a pure source, preferably a non-animal source.

The skilled artisan may also choose to use one of the many individualized media formulations that have been developed to maximize cell growth, cell viability, and/or recombinant polypeptide production in a particular cultured host cell. The methods according to the current invention may be used in combination with commercially available cell culture media or with a cell culture medium that has been individually formulated for use with a particular cell line. For example, an enriched medium that could support increased polypeptide production may comprise a mixture of two or more commercial media, such as, for instance, DMEM and Ham's F12 media combined in ratios such as, for example, 1:1, 1:2, 1:3, 1:4, 1:5, 1:6, 1:7, 1:8, or even up to 1:15 or higher. Alternatively or in addition, a medium can be enriched by the addition of nutrients, such as amino acids or peptone, and/or a medium (or most of its components with the exceptions noted below) can be used at greater than its usual, recommended concentration, for example at 2×, 3×, 4×, 5×, 6×, 7×, 8×, or even higher concentrations. As used herein, "1×" means the standard concentration, "2×" means twice the standard concentration, etc. In any of these embodiments, medium components that can substantially affect osmolarity, such as salts, cannot be increased in concentration so that the osmolarity of the medium falls outside of an acceptable range. Thus, a medium may, for example, be 8× with respect to all components except salts, which can be present at only 1×. An enriched medium may be serum free and/or protein free. Further, a medium may be supplemented periodically during the time a culture is maintained to replenish medium components that can become depleted such as, for example, vitamins, amino acids, and metabolic precursors. As is known in the art, different media and temperatures may have somewhat different effects on different cell lines, and the same medium and temperature may not be suitable for all cell lines.

Suitable culture conditions for mammalian cells are known in the art. See e.g. Animal cell culture: A Practical Approach, D. Rickwood, ed., Oxford university press, New York (1992). Mammalian cells may be cultured in suspension or while attached to a solid substrate. Furthermore, mammalian cells may be cultured, for example, in fluidized bed bioreactors, hollow fiber bioreactors, roller bottles, shake flasks, or stirred tank bioreactors, with or without microcarriers, and operated in a batch, fed batch, continuous, semi-continuous, or perfusion mode.

The methods according to the present invention may be used to improve the production of recombinant polypeptides in both single phase and multiple phase culture processes. In a single phase process, cells are inoculated into a culture environment and the disclosed methods are employed during the single production phase. In a multiple stage process, cells are cultured in two or more distinct phases. For example cells may be cultured first in a growth phase, under environmental conditions that maximize cell proliferation and viability, then transferred to a production phase, under conditions that maximize polypeptide production. The growth and production phases may be preceded by, or separated by, one or more transition phases. In multiple phase processes the methods according to the present invention are employed at least during the production phase. A growth phase may occur at a higher temperature than a production phase. For example, a growth phase may occur at a first temperature from about 35° C. to about 38° C., and a production phase may occur at a second temperature from about 29° C. to about 36° C., optionally from about 30° C. to about 33° C. Chemical inducers of polypeptide production, such as, for example, caffeine, butyrate, and HMBA, may be added at the same time as, before, and/or after a temperature shift. If inducers are added after a temperature shift, they can be added from one hour to five days after the temperature shift, optionally from one to two days after the temperature shift.

After induction using the methods of the invention, the resulting expressed polypeptide can then be collected. In addition, the polypeptide can purified, or partially purified, from such culture or component (e.g., from culture medium or cell extracts or bodily fluid) using known processes. By "partially purified" means that some fractionation procedure, or procedures, have been carried out, but that more polypeptide species (at least 10%) than the desired polypeptide is present. By "purified" is meant that the polypeptide is essentially homogeneous, i.e., less than 1% contaminating polypeptides are present. Fractionation procedures can include but are not limited to one or more steps of filtration, centrifugation, precipitation, phase separation, affinity purification, gel filtration, ion exchange chromatography, hydrophobic interaction chromatography (HIC; using such resins, as phenyl ether, butyl ether, or propyl ether), HPLC, or some combination of above.

For example, the purification of the polypeptide can include an affinity column containing agents which will bind to the polypeptide; one or more column steps over such affinity resins as concanavalin A-agarose, heparin-TOYOPEARL® (Toyo Soda Manufacturing Co. Ltd., Japan) or Cibacrom blue 3GA SEPHAROSE® (Pharmacia Fine Chemicals, Inc., New York); one or more steps involving elution; and/or immunoaffinity chromatography. The polypeptide can be expressed in a form that facilitates purification. For example, it may be expressed as a fusion polypeptide, such as those of mialtose binding polypeptide (MBP), glutathione-S-transferase (GST), or thioredoxin (TRX). Kits for expression and purification of such fusion polypeptides are commercially available from New England BioLab (Beverly, Mass.), Pharmacia (Piscataway, N.J.) and InVitrogen, respectively. The polypeptide can be tagged with an epitope and subsequently purified by using a specific antibody directed to such epitope. One such epitope (FLAGS is commercially available from Kodak (New Haven, Conn.). It is also possible to utilize an affinity column comprising a polypeptide-binding protein, such as a monoclonal antibody to the recombinant polypeptide, to affinity-purify expressed polypeptides. Other types of affinity purification steps can be a Protein A or a Protein G column, which affinity agents bind to proteins that contain Fc domains. Polypeptides can be removed from an affinity column using conventional techniques, e.g., in a high salt elution buffer and then dialyzed into a lower salt buffer for use or by changing pH or other components depending on the affinity matrix utilized, or can be competitively removed using the naturally occurring substrate of the affinity moiety.

The desired degree of final purity depends on the intended use of the polypeptide. A relatively high degree of purity is desired when the polypeptide is to be administered in vivo, for example. In such a case, the polypeptides are purified such that no polypeptide bands corresponding to other polypeptides are detectable upon analysis by SDS-polyacrylamide gel electrophoresis (SDS-PAGE). It will be recognized by one skilled in the pertinent field that multiple bands corresponding to the polypeptide can be visualized by SDS-PAGE, due to differential glycosylation, differential post-translational processing, and the like. Optionally, the polypeptide of the invention is purified to substantial homogeneity, as indicated by a single polypeptide band upon analysis by SDS-PAGE. The polypeptide band can be visualized by silver staining, Coomassie blue staining, or (if the polypeptide is radiolabeled) by autoradiography.

The invention also optionally encompasses further formulating the polypeptides. By the term "formulating" is meant that the polypeptides can be buffer exchanged, sterilized, bulk-packaged, and/or packaged for a final user. For purposes of the invention, the term "sterile bulk form" means that a formulation is free, or essentially free, of microbial contamination (to such an extent as is acceptable for food and/or drug purposes), and is of defined composition and concentration. The term "sterile unit dose form" means a form that is appropriate for the customer and/or patient administration or consumption. Such compositions can comprise an effective amount of the polypeptide, in combination with other components such as a physiologically acceptable diluent, carrier, or excipient. The term "physiologically acceptable" means a non-toxic material that does not interfere with the effectiveness of the biological activity of the active ingredient(s).

Formulations suitable for administration include aqueous and non-aqueous sterile injection solutions which may contain anti-oxidants, buffers, bacteriostats, and solutes which render the formulation isotonic with the blood of the recipient; and aqueous and non-aqueous sterile suspensions which may include suspending agents or thickening agents. The polypeptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants, and/or carriers. Suitable formulations for pharmaceutical compositions include those described in *Remington's Pharmaceutical Sciences*, 16th ed. 1980, Mack Publishing Company, Easton, Pa. In addition, such compositions can be complexed with polyethylene glycol (PEG), metal ions, or incorporated into polymeric compounds such as polyacetic acid, polyglycolic acid, hydrogels, dextran, etc., or incorporated into liposomes, microemulsions, micelles, unilamellar or multi-lamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871, 4,501,728, 4,837,028, and 4,737,323. Such compositions will influence the physical state, solubility, stability, rate of in vivo release, and rate of in vivo clearance, and are thus chosen according to the intended application, so that the characteristics of the carrier will depend on the selected route of administration. Sustained-release forms suitable for use include, but are not limited to, polypeptides that are encapsulated in a slowly-dissolving biocompatible polymer (such as the alginate microparticles described in U.S. Pat. No. 6,036,978), admixed with such a polymer (including topically applied hydrogels), and or encased in a biocompatible semi-permeable implant.

The invention having been described, the following examples are offered by way of illustration, and not limitation.

EXAMPLE 1

Comparison of the Inducing Activity of Caffeine and Butyrate at 31° C.

In this experiment, caffeine (at concentrations from 0.5 to 2.0 mM) was compared to sodium butyrate for its ability to induce expression of a recombinant polypeptide. A CHO cell production line genetically engineered to express TNFR:Fc (cell line #5) was used to test the effectiveness of caffeine as an inducing agent. CHO cells were grown in spinner flasks at 37° C. using serum-free growth medium containing methotrexate. When the appropriate cell mass was obtained, the cells were placed into induction conditions by a five minute centrifugation at 1000×g, followed by replacement of the growth medium with serum-free medium without methotrexate. The cells, at initial cell densities of $2 \times 10^6$ cells/ml in 20 ml, were placed in 125 ml plastic Erlenmeyer flasks with plug seal caps and placed on shaker platforms in incubators set to the appropriate temperatures. Cell viability and number were monitored by haemocytometer counting using trypan blue dye. Recombinant polypeptide titers were assessed by ELISA-based assays.

For this cell line, 0.2 mM was known to be the optimal concentration of sodium butyrate for induction.

Accordingly, 0.2 mM sodium butyrate was compared against the inducing effects of 0.5, 1.0, and 2.0 mM caffeine. A flask containing no inducing compound was also included. The shaker flasks were incubated in this induction phase for 5 days at 31° C. in incubators without carbon dioxide control.

After 5 days in culture, cell viabilities for all of the tested conditions were very similar and ranged between 75 and 85%. The highest relative protein titer (in µg/ml), which was about 1.15 times the titer of the control culture without inducers, and relative productivity (in µg protein/$10^6$ cells/day), which was about 1.3 times the productivity of the control culture, was exhibited by the cells that were induced with 1 mM caffeine. Cells induced with 0.2 mM butyrate produced about 1.11 times the total protein (in µg/ml) produced by the control culture at a rate (in µg protein/$10^6$ cells/day) that was about 1.07 times the rate of control cultures. Similar protein titers were observed in the cells induced with 0.5 mM caffeine, although these cultures had slightly higher rates of production. At caffeine concentrations of 2 mM, protein titer was similar to that observed with no inducing agent, although the rate of productivity per cell was higher.

These results indicate that caffeine can be used as an inducing agent and can induce product titers equal or exceeding those observed using sodium butyrate as an inducing agent. In addition, further experimental data was obtained which indicated that recombinant polypeptide produced using caffeine was equal in product quality (e.g., glycosylation, folding, and amino acid composition) to that produced using sodium butyrate.

EXAMPLE 2

Induction of Recombinant Polypeptide Expression in Cell Line #9

In this experiment, the effect of caffeine (at concentrations from 0 to 1.4 mM) on the induction of expression of a different recombinant polypeptide, a soluble form of the IL-1 receptor type II, in a second CHO cell line (cell line #9) was examined.

CHO cells were grown in spinner flasks at 37° C. using serum-free growth medium containing methotrexate. When the appropriate cell mass was obtained, spent medium was removed by a five minute centrifugation at 1000×g and replaced with production medium without methotrexate. The cells, with initial cell densities of $2 \times 10^6$ cells/ml in 20 ml, were placed in 125 ml plastic Erlenmeyer flasks with plug seal caps. The following caffeine concentrations were tested: 0, 0.6, 0.8, 1.0, 1.2, and 1.4 mM caffeine. The flasks were then incubated in this induction phase for 5 days at 31° C. in incubators without carbon dioxide control. Cell viability and number were monitored by haemocytometer counting using trypan blue dye. Recombinant polypeptide titers were assessed by ELISA-based assays. Each induction assessment experiment was carried out for 5 days.

Figure 2:
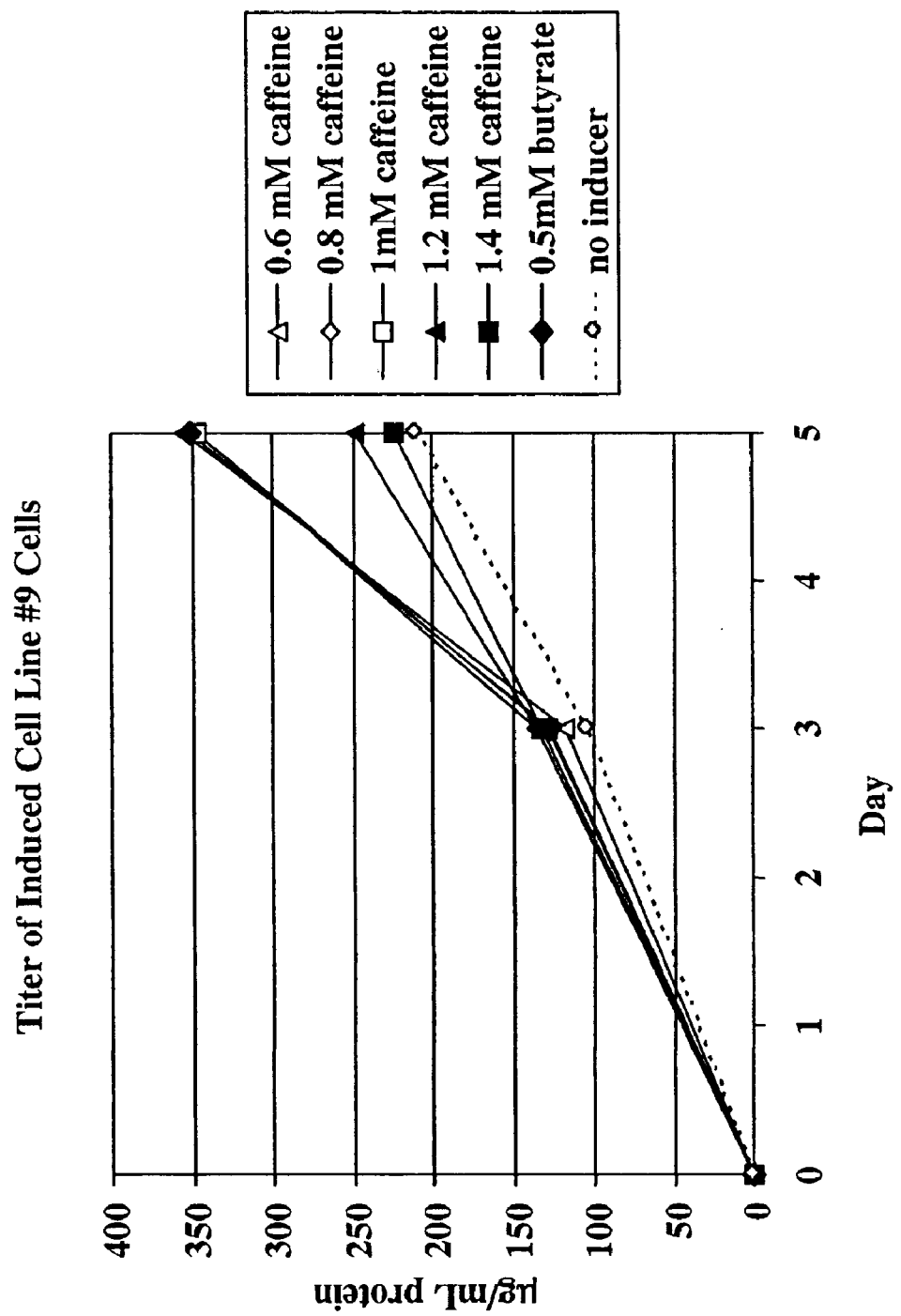
FIG. 2 shows the micrograms of protein per milliliter of cell culture, i.e., protein titer, under the indicated conditions at 31° C. for the #9 CHO cell line as a function of days in culture.
Figure 3:
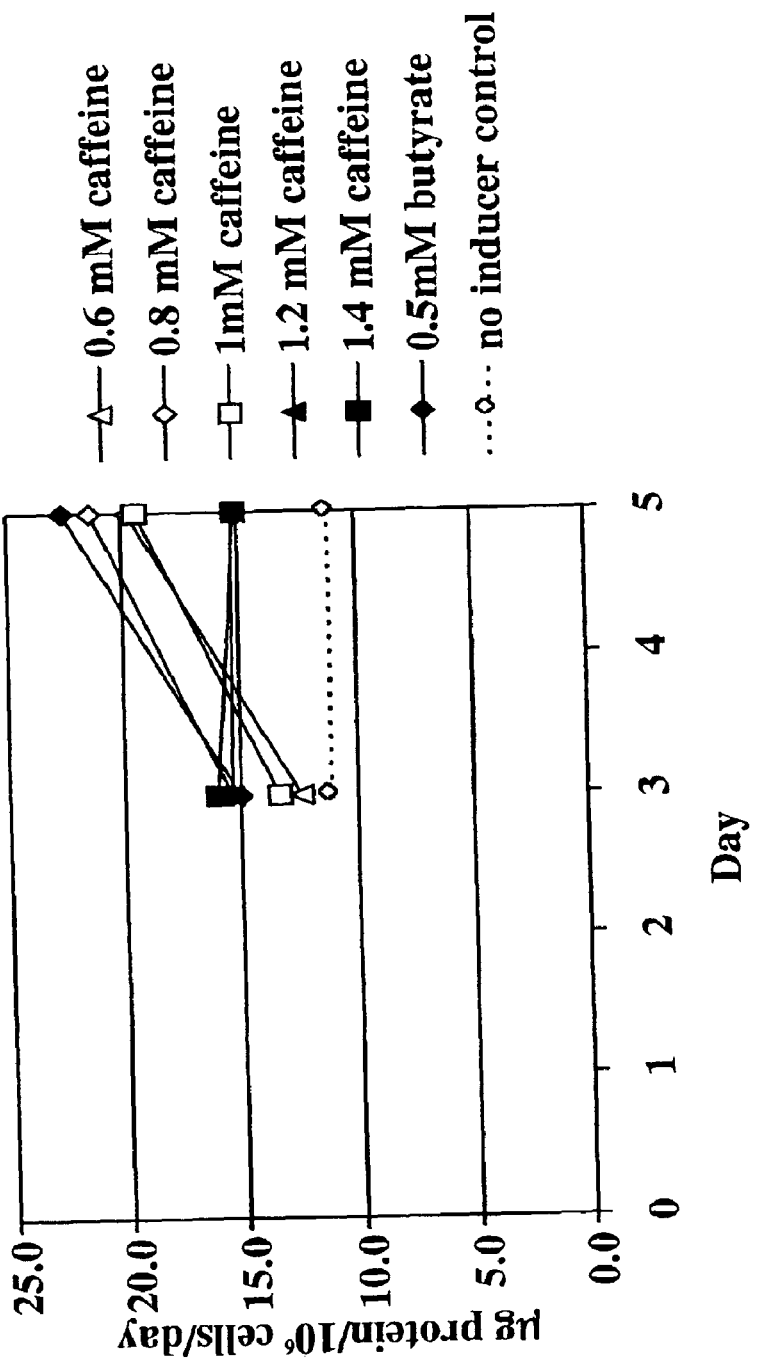
FIG. 3 shows the micrograms of protein per $10^6$ cells per day under the indicated conditions at 31° C. for #9 CHO cell line as a function of days in culture.

After 5 days in culture, cell viability for most of the tested conditions was similar and averaged around 85%. FIG. 1. For the flask induced with 1.4 mM caffeine, 67% cell viability was observed after 5 days. Similar protein titers were observed using 0.6 mM, 0.8 mM, and 1.0 mM caffeine, that is, about 350 µg/mL, which is equal to the titer observed for 0.5 mM butyrate. FIG. 2. Since 0.6 mM is the lowest caffeine concentration tested, these data do not exclude the possibility that even lower concentrations of caffeine might give equal or better results. The highest productivity (in µg protein/$10^6$ cells/day) observed for a caffeine-induced culture was in the 0.8 mM caffeine culture. FIG. 3. At higher levels of caffeine, i.e., 1.2 and 1.4 mM, protein titers were comparable to the negative control (no inducing agent), although productivity on a per cell basis was somewhat higher. FIGS. 2 and 3.

EXAMPLE 3

Induction Of Recombinant Polypeptide Expression In Cell Line #60

In this experiment, the use of caffeine to induce recombinant production from a third CHO cell line (cell line #60) expressing a third recombinant product, a human antibody that recognizes epidermal growth factor receptor, was analyzed. For this cell line, the inducing effects of 0, 0.5, 1.0, 1.5, and 2.0 mM caffeine were tested, and the experiment was conducted as in the previous experiment except that the induction phase was performed at 36° C.

At day 5, the flask of cells with no inducer and the flask of cells induced with 0.5 mM caffeine exhibited the highest cell viabilities (about 76%) of all the conditions. Viabilities of cultures containing 1.0 mM and 1.5 mM caffeine were about 68% and 60%, respectively. Cultures containing 0.75 mM butyrate or 2.0 mM caffeine were about 51% viable. Thus viability, overall, was lower than that seen in cell line #9 at 5 days, an effect that might be attributed to a variety of factors including the difference in temperature and/or cell line differences. A clear dose-response was observed with higher caffeine concentrations leading to lower cell viabilities.

The highest day 5 protein titer was observed in cells induced by 0.5 mM caffeine (305 µg/ml), which was about 111% of the titer of the control culture with no inducer. Generally, the titer of recombinant polypeptide was less as caffeine concentrations increased above 0.5 mM. Productivity (in µg protein/$10^6$ cells/day) appeared to be linked to caffeine concentration, with the highest productivity obtained from cells induced with 2.0 mM caffeine and a lower level of productivity obtained from the cells induced with lower caffeine concentrations. Since a 0.5 mM was the lowest caffeine concentration tested as well as the most effective concentration tested for the induction of protein production, these data do not exclude the possibility that a lower concentration of caffeine might be equally or more effective as an inducer of cell line #60 incubated at 36° C.

This experiment, along with those described in Examples 1 and 2, demonstrates that the ability of caffeine to induce recombinant polypeptide expression is not cell line-specific and that favorable cell viability is maintained in caffeine's presence. In addition, caffeine can be used in an induction or production phase implemented at temperatures from 31° C. to 36° C. However, these data also indicate differences between cell lines in how effectively caffeine induces the synthesis of a recombinant protein. For example, induction of cell line #9 with caffeine is more effective than induction of cell line #60. Compare Example 2 and FIG. 2 to Example 3.

EXAMPLE 4

Optimization of Induction for Cell Line #60

The purpose of this experiment was to test ranges of temperature and caffeine concentrations in shake flasks in order to optimize the induction conditions for the cell line #60.

Materials and Methods. Twelve shaker flasks were set up under the conditions described in Table 1.

TABLE 1

Caffeine Concentrations and Temperatures of Samples

| Flask Number | Temperature (° C.) | Caffeine (mM) |
|---|---|---|
| 1 | 36 | 0 |
| 2 | 36 | 0.5 |
| 3 | 36 | 1.0 |
| 4 | 36 | 1.5 |
| 5 | 36 | 2.0 |
| 6 | 36 | 2.5 |
| 7 | 37 | 0 |
| 8 | 37 | 0.5 |
| 9 | 37 | 1.0 |
| 10 | 37 | 1.5 |
| 11 | 37 | 2.0 |
| 12 | 37 | 2.5 |

Cells were collected via centrifugation from a spinner culture of cell line #60 ($26.85 \times 10^5$ cells/ml, 95.2% viable) and inoculated into a 575 ml spinner flask at $2 \times 10^6$ cells/ml in serum-free production medium. The culture was then aliquoted into twelve shake flasks. Caffeine was added according to the experimental plan described in Table 1. The shake flasks were incubated at the designated temperatures for 7 days. Samples were taken on days 3, 5 and 7. Cell density and viability were measured using an automated system of cell counting that employs trypan blue staining to determine viability (the Cell Density Examination System or Cedex, developed by innovatis GmbH, Bielefeld, Germany). Glucose and lactate measurements were taken with the Yellow Springs Instruments 2700 Select (available from Yellow Springs Instruments, Yellow Springs, Ohio, USA). Glucose was added on demand to maintain a concentration of >2 g/l. $CO_2$ and external pH were measured using the Ciba-Corning 248 blood gas analyzer (available from Bayer Diagnostics, Tarryton, N.Y., USA). Protein titers were determined via a pre-purification of the antibody on a Protein A column followed by a measurement of the absorbance of the protein bound and eluted from the column at 280 nanometers. Cumulative viable cell densities (CVCDs) were calculated as follows: the CVCD for day 1 is the number of viable cells per milliliter of culture as measured on day 1; the CVCD for day 2 is the number of viable cells per milliliter of culture as measured on day 2 plus the number of viable cells per milliliter of culture as measured on day 1; the CVCD for day 3 is the number of viable cells per milliliter of culture as measured on day 3 plus the numbers of viable cells per milliliter of culture measured on days 1 and 2; and CVCDs for subsequent days are calculated in a similar manner.

Results. Higher CVCDs were achieved in the presence of little or no caffeine. Lower temperature, i.e., 36° C. rather than 37° C. and lower levels of caffeine resulted in higher final viability. Caffeine at 2.5 mM resulted in cell death and termination of the cultures. Over the rest of the concentration range tested, increased levels of caffeine resulted in increased cumulative specific productivity (Cum Qp), with the highest level being almost 30 µg/$10^6$ cells/day. Cultures containing the highest levels of caffeine resulting in viable cultures (2 mM), while having a high Cum Qp, had a low CVCD, indicating that 2 mM caffeine decreased cell viability but increased the productivity of remaining viable cells. However, protein titers of cultures induced with 2 mM caffeine were lower than for uninduced cultures at 7 days at both temperatures.

The highest protein titers resulted at the low to intermediate levels of caffeine for both temperatures. The highest day 7 titer was observed in the culture grown at 36° C. in the presence of 0.5 mM caffeine, and its titer was about 124% of the titer seen in a control culture grown at 36° C. for 7 days without inducers. Day 7 titers of 36° C. cultures grown in the presence of 1.0 mM and 1.5 mM caffeine were about 116% and 111% of control levels, respectively. The day 7 titers of cultures grown at 37° C. in the presence of 0.5 mM, 1.0 mM, and 1.5 mM caffeine were about 110%, 112%, and 109%, respectively, of the 37° C. no inducer control culture. Together, these data indicate that induction of cell line #60 was more effective at 36° C. than it was at 37° C. Day 7 titers of control cultures without inducers grown at 36° C. and 37° C. were comparable. Thus, as in Example 3, the lowest concentration of caffeine tested led to the highest protein titers at 36° C., suggesting the possibility that even lower concentrations might produce equal or higher titers.

In summary, induction with caffeine increased specific productivity and titer at both 36° C. and 37° C. Titers were modestly higher at 36° C. than at 37° C. despite lower Cum Qp values because of higher CVCDs and viability at the lower temperature. Based on cell performance and productivity, caffeine can be used to induce production from this cell line.

EXAMPLE 5

Induction Effects for Compounds Related to Caffeine in Cell Line #9

Since the above experiments showed that caffeine as an inducing agent increased titers of recombinant polypeptide between about 9% and about 67%, additional experiments were performed with other xanthine derivatives to test their inducing ability. Based upon the structure of xanthine, a variety of compounds were modeled and chosen for testing. These include 3-isobutyl-1-methylxanthine, theophylline, theobromine, pentoxifylline, and aminophylline, the structures of which are illustrated below.

TABLE 2

Xanthine Derivatives

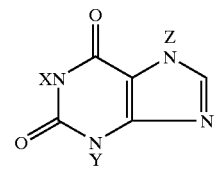

| Compound | X | Y | Z |
|---|---|---|---|
| caffeine | methyl | methyl | methyl |
| 3-isobutyl-1-methylxanthine (IBX) | methyl | isobutyl | hydrogen |
| theophylline | methyl | methyl | hydrogen |
| theobromine | hydrogen | methyl | methyl |
| pentoxifylline | 5-oxyhexyl | methyl | methyl |

Aminophylline is theophylline compound with 1,2-ethylenediamine (2:1) dihydrate.

These xanthine derivatives, including some combinations, were tested on cell line #9 in a shake-flask format (20 ml in 125 ml shake flasks) as described above for Examples 1 and 2. To dissolve 3-isobutyl-1-methylxanthine (IBX), it was solubilized in water heated to almost the boiling point, and quickly added to the flasks before it precipitated. Alternatively, IBX was dissolved in DMF. The induction phase of the cell culture was carried out for 6 days at 31° C., and samples were removed for analysis at 3 day and 6 day timepoints. The protein titers from each shake flask are shown in Table 3.

TABLE 3

Recombinant Polypeptide Titer Under Various Inducing Conditions

| Condition | Titer (µg/ml) Day 3 | Titer (µg/ml) Day 6 |
|---|---|---|
| 0.6 mM caffeine + 0.5 mM butyrate | 120 | 280 |
| 0.1 mM theobromine | 90 | 270 |
| 0.5 mM theobromine | 100 | 260 |
| 1 mM theobromine | 100 | 260 |
| 0.1 mM aminophylline | 110 | 260 |
| 0.5 mM aminophylline | 120 | 250 |
| 1 mM aminophylline | 100 | 200 |
| 0.1 mM pentoxyphylline | 110 | 320 |
| 0.5 mM pentoxyphylline | 130 | 380 |
| 1 mM pentoxyphylline | 130 | 400 |
| 0.3% DMF + 0.5 mM IBX | not determined | 340 |
| 0.3% DMF | 120 | 330 |
| 0.5 mM IBX | 150 | 420 |
| 0.5 mM IBX + 0.6 mM caffeine | 130 | 370 |
| 0.1 mM IBX + 0.6 mM caffeine | 140 | 390 |
| 0.1 mM IBX + 0.6 mM caffeine + 0.5 mM butyrate | 130 | 280 |
| 0.1 mM IBX + 0.6 mM caffeine + 0.3% DMF | 150 | 390 |
| 0.2 mM caffeine | 150 | 400 |
| 0.6 mM caffeine | 120 | 320 |
| 0.5 mM butyrate | 100 | 220 |
| NO INDUCER | 100 | 290 |

Several conclusions can be made from this data. Production from the flask induced with 0.5 mM IBX was even better than caffeine, and the 3 flasks containing pentoxyphylline also gave promising results. Titers of pentoxyphylline-induced cultures increased with increasing dose and were higher than the tier of the no inducer control culture. Additionally, some combinations of different xanthine derivatives, as well as different xanthine derivatives with other inducing agents (e.g., butyrate and/or DMF) yielded protein titers above control levels. Theobromine and aminophylline did not induce protein titers above that seen in the no inducer control culture. The highest protein liters obtained when caffeine was used as an inducer were obtained at the lowest concentration tested, that is, 0.2 mM caffeine. As explained above, such a result leaves open the possibility that even lower concentrations of caffeine may be effective. Finally, unlike in Example 2 (FIG. 2), butyrate does not induce increased protein titer over that seen in a culture with no inducer.

EXAMPLE 6

Induction of Cell Line #60 by Various Inducing Agents at 37° C.

This experiment was done in shaken Erlenmeyer flasks as described above in Examples 1 and 2, except that the flasks were incubated for 5 days at 37° C., rather than at 31° C., and cell line #60 was used. As a control, one flask without inducers was grown at 31° C. The titer of recombinant polypeptide in the medium was assayed after 5 days. Xanthine derivatives tested included caffeine (at 0.5 mM), theobromine (at 0.1 mM, 0.5 mM, and 1.0 mM), 3-isobutyl-1-methylxanthine (IBX, at 0.05 mM, 0.1 mM, and 0.15 mM), and pentoxyphylline (at 0.1 mM, 0.5 mM, and 1.0 mM). In addition, butyrate, some combinations of inducers, and the non-xanthine compound papaverine were tested.

The 31° C. control culture yielded low protein titers compared to the 37° C. control culture, probably due to the preference of cell line #60 for higher temperatures. Theobromine at a concentration of 0.1 mM increased protein titer over that seen in the 37° C. control culture, but was counterproductive at higher concentrations (0.5 mM and 1.0 mM). Neither caffeine, IBX, or pentoxyphylline increased protein titers above that seen in a control culture with no inducers. Protein titer was inversely proportional to theobromine, IBX, and pentoxyphylline concentrations in the ranges tested. Interestingly, cell line #9 (Table 3, Example 5) showed increased protein titers with increasing pentoxyphylline concentrations within this same range, highlighting the variability in the responses of different cell lines incubated at different temperatures to inducing agents. As in other experiments (see Example 3), 0.5 mM caffeine appears to be a better inducer than 0.5 mM butyrate for cell line #60, although both failed to increase protein titer over that seen in the control culture with no inducing agent in this experiment. In a previous experiment, caffeine had induced slightly higher protein production than that seen in a control culture at 37° C. at day 7 (about 110% of the titer seen in the control culture), although a greater induction was observed at 36° C. Example 4. The failure of caffeine to induce increased protein production in this experiment may be explained by a variety of factors such as experimental variability, the small size of the positive effect at 37° C. in cell line #60, and/or the possibility that 0.5 mM may not be an optimum caffeine concentration for induction of cell line #60 at 37° C.

EXAMPLE 7

Production of RANK:Fc in the Presence of Varying Amounts of HMBA

Nucleic acids encoding RANK:Fc inserted into a suitable vector (as described in International Application WO 01/36637) were introduced into CHO cells. About 2 million cells from a stably transformed line propagated at 37° C. were inoculated into 20 milliliters of medium at 31° C., either without HMBA or in the presence of varying concentrations of HMBA, as indicated in Table 4. Cells were grown for a total of 5 days in shaker flasks. Thereafter, all medium was harvested. The number of cells present in the culture was determined by staining with trypan blue and counting the cells in a hemocytometer. The titer of RANK:Fc per milliliter of harvested medium was determined by purifying RANK:Fc by Protein A high performance liquid chromatography (HPLC) and subsequently measuring absorbance at 280 nanometers. An average number of cells in the culture was calculated by averaging the starting and ending cell numbers. Specific productivity was determined from the total number of micrograms of RANK:Fc produced, an average cell number (calculated as described above), and the number of days of growth. Data from this experiment are shown in Table 4.

TABLE 4

Effects of Varying Concentrations of HMBA on Protein Titer and Specific Productivity

| HMBA concentration (mM) | Specific productivity (µg/10$^6$ cells/day) | Titer of RANK:Fc (µg/ml) |
|---|---|---|
| 0 | 17.1 | 272 |
| 0.1 | 19.1 | 243 |
| 0.5 | 19.5 | 347 |
| 2.0 | 23.9 | 444 |

These data indicate that the addition of HMBA at concentrations of 0.5 or 2.0 mM had positive effects on polypeptide production and specific productivity.

EXAMPLE 8

Production of RANK:Fc in the Presence of HMBA, Caffeine, and/or Butyric Acid

Nucleic acids encoding RANK:Fc inserted into a suitable vector (as described in International Application WO 01/36637) were introduced into CHO cells. About 2 million cells from a stably transformed line propagated at 37° C. were inoculated into 20 milliliters of serum-free medium at 31° C. without inducers or in the presence of of HMBA and/or caffeine and/or butyric acid, as indicated in Table 5. Cells were grown for a total of 5 days in a shaker flask. Thereafter, all medium was harvested. The number of cells present in the culture, the titer of RANK:Fc per milliliter of harvested medium, and specific productivity were determined as described above in Example 7. Data from this experiment are shown in Table 5.

TABLE 5

Effects of Caffeine, HMBA, and Butyric Acid Singly and In Combination on Protein Titer and Specific Productivity

| Inducer | Specific productivity (µg/10⁶ cells/day) | Titer of RANK:Fc (µg/ml) |
| --- | --- | --- |
| None | 14.8 | 261 |
| HMBA (2 mM) | 22.8 | 410 |
| Caffeine (1 mM) | 23.6 | 362 |
| Butyric acid (0.5 mM) | 31.6 | 476 |
| HMBA (2mM) + Caffeine (1 mM) + butyric acid (0.5 mM) | 46.7 | 553 |

These data indicate that the addition either caffeine (at 1 mM), butyric acid (at 0.5 mM), or HMBA (at 2 mM) had positive effects on both polypeptide production and specific productivity and that the combination of butyric acid, caffeine, and HMBA (at the concentrations mentioned above) had greater positive effects than any of these compounds alone.

EXAMPLE 9

Production of Type II IL-1 Receptor in the Presence of HMBA in a Bioreactor

Nucleic acids encoding a type II IL-1 receptor inserted into a suitable vector were introduced into CHO cells. About 500 thousand cells from a stably transformed line were inoculated into a one liter of serum-free medium in a bioreactor. Cells were grown for two days at 37° C. Thereafter, cells were shifted to 31° C., either without HMBA or in the presence of 2 mM HMBA, and grown for 12 more days. Thereafter, all medium was harvested. The titer of type II IL-1 receptor per milliliter of harvested medium was determined by purification by reverse phase HPLC followed by the measurement of absorbance at 280 nanometers. Data from this experiment are shown in Table 6 as a percentage of the average of the protein titers obtained from the two samples without HMBA rounded to the nearest whole number.

TABLE 6

Effects of 2 mM HMBA on Protein Titer

| Inducer | Relative Titer of type II IL-1 Receptor (percent of average of samples without HMBA) |
| --- | --- |
| None | 99% |
| None | 101% |
| HMBA (2 mM) | 120% |
| HMBA (2 mM) | 125% |

These data show that bioreactor cultures shifted to 31° C. after an initial 37° C. growth phase produced more type II IL-1 receptor if HMBA was added at the time of temperature shift than if it wasn't. These data further suggest that the invention can be useful for producing a variety of polypeptides in a variety of cell lines and that the mechanics of how the cells are grown, for example, in a shaker flask versus in a bioreactor, are not critical.

EXAMPLE 10

Production of an Antibody Against Murine IL-4 Receptor in CHO Cells

The experiment described below tests the effects of using either sodium butyrate or HMBA as an inducer in still another cell line at various temperatures.

Figure 4:
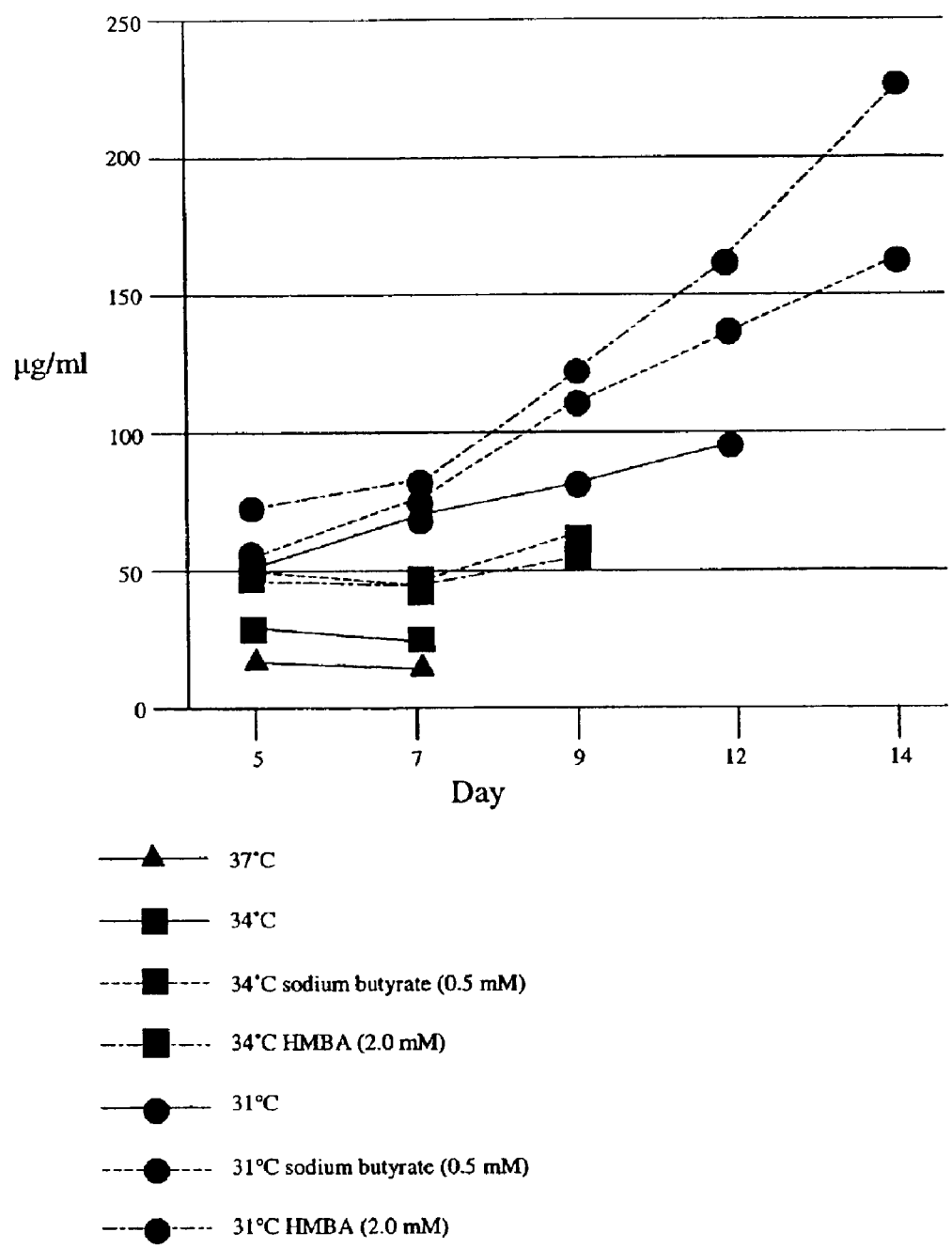
FIG. 4 shows a graph displaying the concentration of an antibody against murine IL-4 receptor recovered from medium as a function of days of growth of a CHO cell line comprising a vector encoding the antibody at the stated temperatures in the presence or absence of HMBA or sodium butyrate. Markings are as follows: —▲—, no inducer 37° C.; —■—, no inducer 34° C.; - -■- - -, 0.5 millimolar sodium butyrate 34° C.; - - -■- - -, 2.0 millimolar HMBA 34° C.; —●—, no inducer 31° C.; - - -●- - -, 0.5 millimolar sodium butyrate 31° C.; and - - - ● - - -, 2.0 millimolar HMBA 31° C.

Nucleic acids encoding an antibody against a murine IL-4 receptor inserted into a suitable vector were introduced into CHO cells. About two million cells from a stably transformed line propagated at 37° C. were inoculated into 20 milliliters of medium at the temperatures indicated in FIG. 4 and in the presence or absence of HMBA (2 mM) or sodium butyrate (0.5 mM), as indicated in FIG. 4. Cells were grown for a maximum of 14 days in a shaker flask. Aliquots were removed at the times indicated in FIG. 4, and the titer of the antibody (in micrograms per milliliter of harvested medium) was determined by enzyme-linked immunosorbent assay (ELISA), a method well known in the art. See e.g. Reen (1994), Enzyme-Linked Immunosorbent Assay (ELISA), in Basic Protein and Peptide Protocols, Methods Mol. Biol. 32:461–466. The results are shown in FIG. 4. These data indicate that growth at 31° C. resulted in the production of more antibody for a longer time than growth at either 34° C. or 37° C. when medium was harvested at 7 days or later. These data also indicate that both HMBA and sodium butyrate, individually, enhanced production of the antibody and that HMBA did so to a greater extent than did sodium butyrate at 31° C.

EXAMPLE 11

Production of TNFR:Fc in CHO Cells

Nucleic acids encoding human TNFR:Fc in a suitable vector were introduced into CHO cells. About 3±0.5×10⁶ cells from a stably transformed cell line propagated at 37° C. were introduced into each of three 1 liter bioreactors and cultured at 32.5° C. in an enriched, serum-free medium. Sodium butyrate (0.5 mM) was added to all three cultures, and HMBA (2 mM) was added to two of the cultures ("day 1+HMBA") one day after the shift to 32.5° C. Cells were incubated for a total of 11 days at 32.5° C. Medium was harvested, and protein titer was determined by measuring optical density at 280 nanometers following a prepurification using Protein A POROS® Perfusion Chromatography™ (Applied Biosystems, Foster City, Calif., USA). These results are shown in Table 7 as a percentage of the titer obtained from the sample with no HMBA ("day 1") rounded to the nearest whole number.

TABLE 7

Effects of the Timing of Addition of Inducers

|  | Relative Titer TNFR:Fc (percent of the day 0 titer) |
| --- | --- |
| day 1 | 100% |
| day 1 + HMBA | 131% |
| day 1 + HMBA | 110% |

These data indicate that the addition of HMBA increased the titer of TNFR:Fc produced by these cultures when added one day after a temperature shift to 32.5° C. These data, together with the data in previous examples, indicate that addition of HMBA can increase protein titer when it is added at the time of or after a shift to a lower temperature.

The foregoing description of specific embodiments reveals the general nature of the invention so that others can readily modify and/or adapt such embodiments for various applications without departing from the generic concepts presented herein. Any such adaptions or modifications are intended to be embraced within the meaning and range of equivalents of the disclosed embodiments. Phraseology and terminology employed herein are for the purpose of description and not of limitation. All references cited herein are hereby incorporated by reference in their entirety.

What is claimed is:

1. A method for producing a polypeptide comprising:
culturing a mammalian cell line in a growth phase followed by a production phase, wherein the production phase occurs at a temperature of less than 37° C.; and
adding to the culture medium during the production phase a xanthine derivative;
wherein the addition of the xanthine derivative increases production of the polypeptide; and
wherein the mammalian cell line is selected from the group consisting of a mammalian cell line that has been genetically engineered to produce the polypeptide and a hybridoma cell line that produces an antibody.

2. The method of claim 1,
wherein the mammalian cell line has been transformed with a recombinant vector encoding the polypeptide, and
wherein the recombinant vector comprises a CMV promoter.

3. The method of claim 1, wherein the xanthine derivative is caffeine at a concentration from about 0.01 millimolar to about 3.0 millimolar.

4. The method of claim 1, wherein the polypeptide is a recombinant fusion polypeptide.

5. The method of claim 1, wherein the antibody polypeptide is a human or humanized antibody.

6. The method of claim 1, wherein the production phase occurs at a temperature from about 29° C. to about 36° C.

7. The method of claim 1, wherein the concentration of each xanthine derivative added to the culture is from about 0.001 millimolar to about 3 millimolar.

8. The method of claim 1, wherein the xanthine derivative is selected from the group consisting of caffeine, 3-isobutyl-1-methylxanthine, theobromine, and pentoxyphylline.

9. The method of claim 1, wherein at least two different xanthine derivatives are added.

10. The method of claim 9, wherein the two different xanthine derivatives are caffeine and 3-isobutyl-1-methylxanthine.

11. The method of claim 1, wherein the mammalian cell line is a CHO cell line.

12. The method of claim 11, wherein the CHO cell line is exposed to the xanthine derivative or derivatives for at least about 5 days.

13. The method of claim 1, wherein the medium used during the production phase is serum free.

14. The method of claim 1, further comprising collecting the polypeptide from the medium.

15. The method of claim 14, further comprising formulating the polypeptide.

16. The method of claim 1, further comprising multiple additions of the xanthine derivative.

17. The method of claim 1, wherein the medium further comprises a hybrid polar compound.

18. The method of claim 17, wherein the medium further comprises an alkanoic acid.

19. The method of claim 1, wherein the medium further comprises an alkanoic acid.

20. The method of claim 17, wherein the hybrid polar compound is hexamethylene bisacetamide and the xanthine derivative is caffeine.

21. The method of claim 20,
wherein the medium further comprises a salt of butyric acid at a concentration from about 0.1 millimolar to about 2 millimolar,
wherein hexamethylene bisacetamide is at a concentration from about 0.1 millimolar to about 5 millimolar, and
wherein caffeine is at a concentration from about 0.01 millimolar to about 5 millimolar.

22. The method of claim 17, wherein the mammalian cell line is cultured at a temperature from about 29° C. to about 36° C.

23. The method of claim 22, wherein the mammalian cell line is cultured at a temperature from about 30° C. to about 33° C.

24. The method of claim 22,
wherein the mammalian cell line is cultured in the growth phase at a first temperature from about 35° C. to about 38° C. before it is shifted to the production phase at a second temperature from about 29° C. to about 36° C. and
wherein the hybrid polar compound and the xanthine are added after the shift from the first temperature to the second temperature.

25. The method of claim 18, wherein the mammalian cell line is cultured at a temperature from about 29° C. to about 36° C.

26. A method for producing a recombinant polypeptide comprising:
culturing a CHO cell line that has been genetically engineered to produce the recombinant polypeptide; and
adding to the culture medium at least one xanthine derivative selected from the group consisting of theobromine and caffeine,
wherein the addition of the xanthine derivative increases the production of the recombinant polypeptide.

27. The method of claim 26,
wherein the CHO cell line has been transformed with a recombinant vector encoding the recombinant polypeptide and wherein the recombinant vector comprises a CMV promoter.

28. The method of claim 26, wherein the recombinant polypeptide is a fusion polypeptide.

29. The method of claim 26, wherein the recombinant polypeptide is a human or humanized antibody.

30. The method of claim 26, wherein the concentration of each xanthine derivative added to the culture medium is from about 0.001 millimolar to about 3 millimolar.

31. The method of claim 26, wherein the xanthine derivative is caffeine.

32. The method of claim 26, further comprising collecting the recombinant polypeptide from the medium.

33. The method of claim 32, further comprising formulating the recombinant polypeptide.

34. The method of claim 26, further comprising multiple additions of the xanthine derivative.

35. The method of claim 26, wherein the CHO cell line is cultured at a temperature from about 29° C. to about 36° C.

36. The method of claim 35, wherein the CHO cell line is cultured at a temperature from about 30° C. to about 33° C.

37. The method of claim 35,
wherein the CHO cell line is cultured at a first temperature from about 35° C. to about 38° C. before it is shifted to a second temperature from about 29° C. to about 36° C. and
wherein the xanthine derivative is added after the shift from the first temperature to the second temperature.

38. A culture comprising a CHO cell genetically engineered to produce a polypeptide, a production medium, and a xanthine derivative selected from the group consisting of caffeine, theobromine, and pentoxyphylline.

39. The culture of claim 38, wherein the concentration of each xanthine derivative present is from about 0.01 millimolar to about 3 millimolar.

40. The culture of claim 38, wherein the production medium is serum-free.

41. The culture of claim 38, wherein the culture comprises at least two xanthine derivatives.

42. A method for producing a recombinant polypeptide comprising
culturing a mammalian cell line at a temperature from about 29° C. to about 36° C. and
adding a hybrid polar compound to the culture medium, wherein the mammalian cell line has been genetically engineered to produce the recombinant polypeptide and
wherein the addition of the hybrid polar compound increases the production of the recombinant polypeptide.

43. The method of claim 42, wherein the hybrid polar compound is hexamethylene bisacetamide at a concentration from about 0.1 millimolar to about 20 millimolar.

44. The method of claim 42,
wherein the mammalian cell line is cultured at a first temperature from about 35° C. to about 38° C. before it is shifted to a second temperature from about 29° C. to about 36° C. and
wherein the hybrid polar compound is added is added after the shift from the first temperature to the second temperature.

45. The method of claim 42, wherein the medium further comprises an alkanoic acid at a concentration from about 0.05 millimolar to about 10 millimolar.

46. The method of claim 43, wherein the hexamethylene bisacetamide in the medium is present at a concentration from about 0.1 millimolar to about 5 millimolar.

47. The method of claim 42, wherein the mammalian cell line is cultured at a temperature from about 30° C. to about 33° C.

48. The method of claim 45, wherein
the alkanoic acid is a salt of butyric acid, and
the concentration of the salt of butyric acid is from about 0.1 millimolar to about 2 millimolar.

49. The method of claim 45, wherein
the hybrid polar compound is hexamethylene bisacetamide at a concentration from about 0.1 millimolar to about 5 millimolar, and
the alkanoic acid is a salt of butyric acid at a concentration from about 0.1 millimolar to about 2 millimolar.

50. The method of claim 42, wherein the medium is serum free.

51. The method of claim 42, wherein the medium further comprises a xanthine derivative.

52. The method of claim 51, wherein the xanthine derivative is caffeine.

53. The method of claim 51, wherein the medium further comprises a salt of butyric acid.

54. The method of claim 53, wherein the xanthine derivative is present at a concentration from about 0.01 millimolar to about 3 millimolar and the salt of butyric acid is present at a concentration from about 0.1 millimolar to about 2 millimolar.

55. The method of claim 42, wherein the recombinant polypeptide is a secreted polypeptide.

56. The method of claim 55, further comprising recovering the recombinant polypeptide from the medium.

57. The method of claim 42, wherein the mammalian cell line is a CHO cell line.

58. A method for producing a polypeptide comprising
culturing a mammalian cell line that can express the polypeptide in a growth phase at a first temperature from about 35° C. to about 38° C., and then
culturing the mammalian cell line in a production phase at a second temperature from about 30° C. to 34° C. in a medium comprising a hybrid polar compound.

59. The method of claim 58, wherein the polypeptide is a recombinant polypeptide or an antibody.

60. The method of claim 58, wherein the hybrid polar compound is hexamethylene bisacetamide.

61. The method of claim 58, wherein the medium further comprises an alkanoic acid.

62. The method of claim 61, wherein the hybrid polar compound is hexamethylene bisacetamide and the alkanoic acid is a salt of butyric acid.

63. The method of claim 58, wherein the medium is serum free.

64. The method of claim 58, wherein the hybrid polar compound is added after the shift from the first temperature to the second temperature.

65. The method of claim 58, wherein
the medium further comprises a xanthine derivative at a concentration from about 0.001 millimolar to about 5.0 millimolar and an alkanoic acid at a concentration from about 0.05 millimolar to about 10.0 millimolar and
the hybrid polar compound is hexamethylene bisacetamide at a concentration from about 0.1 millimolar to about 5 millimolar.

66. The method of claim 58, wherein the mammalian cell line is a hybridoma cell line or a CHO cell line.

67. A method for producing a polypeptide comprising culturing mammalian cells that can produce the polypeptide in a medium comprising between about 0.1 millimolar and about 5 millimolar hexamethylene bisacetamide, from about 0.1 millimolar to about 2 millimolar butyric acid, and from about 0.1 millimolar to about 4 millimolar caffeine at a temperature from about 30° C. to about 36° C.

68. The method of claim 67, wherein the polypeptide is selected from the group consisting of RANK:Fc, type II interleukin-1 receptor, TNFR:Fc, CD40 ligand, TRAIL, flt3-ligand, IL-4 receptor, G-CSF, erythropoietin, an antibody, and substantially similar polypeptides.

69. A cell culture comprising a CHO cell line that has been genetically engineered to produce a polypeptide and a production medium comprising hexamethylene bisacetamide, wherein the culture is incubated at a temperature from about 30° C. to 36° C. for at least about 5 days.

* * * * *

UNITED STATES PATENT AND TRADEMARK OFFICE
CERTIFICATE OF CORRECTION

PATENT NO. : 6,872,549 B2  
APPLICATION NO. : 10/400334  
DATED : March 29, 2005  
INVENTOR(S) : Kirk P. Van Ness et al.

It is certified that error appears in the above-identified patent and that said Letters Patent is hereby corrected as shown below:

Column 14, line 63, "arc" should read -- are --.

Column 23, line 22, "(FLAGS" should read -- (FLAG®) --.

Column 29, line 36, "tier" should read -- titer --.

Column 31, line 13, remove the second occurrence of "of".

Column 31, line 38, "addition either" should read -- addition of either --.

Signed and Sealed this

Twenty-sixth Day of December, 2006

JON W. DUDAS  
*Director of the United States Patent and Trademark Office*